United States Patent
Fan et al.

(10) Patent No.: US 10,550,103 B2
(45) Date of Patent: *Feb. 4, 2020

(54) DUAL INHIBITORS OF PARP1 AND CDK

(71) Applicant: Accutar Biotechnology, Brooklyn, NY (US)

(72) Inventors: Jie Fan, Brooklyn, NY (US); Ke Liu, Shanghai (CN)

(73) Assignee: Accutar Biotechnology, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/287,284

(22) Filed: Feb. 27, 2019

(65) Prior Publication Data

US 2019/0202807 A1 Jul. 4, 2019

Related U.S. Application Data

(63) Continuation of application No. 16/235,652, filed on Dec. 28, 2018.

(60) Provisional application No. 62/611,679, filed on Dec. 29, 2017.

(51) Int. Cl.

| | | |
|---|---|---|
| *C07D 487/04* | (2006.01) | |
| *C07D 401/14* | (2006.01) | |
| *C07D 471/04* | (2006.01) | |
| *A61P 35/00* | (2006.01) | |
| *C07D 487/06* | (2006.01) | |
| *C07D 519/00* | (2006.01) | |

(52) U.S. Cl.
CPC ............ *C07D 401/14* (2013.01); *A61P 35/00* (2018.01); *C07D 471/04* (2013.01); *C07D 487/04* (2013.01); *C07D 487/06* (2013.01); *C07D 519/00* (2013.01)

(58) Field of Classification Search
CPC .................................................... C07D 487/04
See application file for complete search history.

(56) References Cited

U.S. PATENT DOCUMENTS

| | | |
|---|---|---|
| 7,151,102 B2 | 12/2006 | Martin et al. |
| 7,449,464 B2 | 11/2008 | Martin et al. |
| 7,855,211 B2 | 12/2010 | Coates et al. |
| 7,981,889 B2 | 7/2011 | Barr Martin et al. |
| 8,143,241 B2 | 3/2012 | Ashworth et al. |
| 8,247,416 B2 | 8/2012 | Menear et al. |
| 8,415,355 B2 | 4/2013 | Brain et al. |
| 8,475,842 B2 | 7/2013 | Bechtold et al. |
| 8,685,980 B2 | 4/2014 | Besong et al. |
| 8,841,312 B2 | 9/2014 | Connors et al. |
| 8,859,562 B2 | 10/2014 | Helleday |
| 8,912,187 B2 | 12/2014 | Martin et al. |
| 2014/0271460 A1 | 9/2014 | Sharpless et al. |
| 2016/0008367 A1 | 1/2016 | Borland et al. |

OTHER PUBLICATIONS

International Search Report and Written Opinion dated Mar. 28, 2019, for PCT/US2018/067947.

*Primary Examiner* — Bruck Kifle
(74) *Attorney, Agent, or Firm* — Cooley LLP

(57) ABSTRACT

Disclosed herein, in various embodiments, are compounds having dual activity as PARP1 and CDK inhibitors, and pharmaceutical compositions comprising the same. In some embodiments, the present disclosure provides for methods of treating diseases or conditions in a subject in need thereof, comprising administering one or more compounds disclosed herein. In some embodiment, the disease is cancer, including breast cancer.

29 Claims, 19 Drawing Sheets

DUAL INHIBITORS OF PARP1 AND CDK

CROSS-REFERENCE TO RELATED APPLICATIONS

This application is a continuation of U.S. application Ser. No. 16/235,652, filed Dec. 28, 2018, which claims the benefit of U.S. Provisional Application No. 62/611,679, filed on Dec. 29, 2017, the entire contents of each of which are herein incorporated by reference in its entirety for all purposes.

FIELD OF INVENTION

The present disclosure provides for compounds, more specifically compounds which have dual activity as PARP1 and CDK inhibitors, and pharmaceutical compositions comprising the same. The present disclosure also provides for methods of treating diseases or conditions in a subject in need thereof, such as cancer, including breast cancer.

BACKGROUND

PARP1 (poly-ADP ribose polymerase-1) is an enzyme that participates in a variety of DNA-related functions including cell proliferation, differentiation, apoptosis, and DNA repair. PARP1 consumes NAD+ and ATP, which can culminate in cell dysfunction or necrosis. PARP1-induced necrosis has been implicated in cancer, stroke, myocardial ischemia, diabetes, diabetes-associated cardiovascular dysfunction, shock, traumatic central nervous system injury, arthritis, colitis, allergic encephalomyelitis, and various other forms of inflammation. PARP1 over-expressions has been correlated with endometrial cancer, BRCA-mutated ovarian cancer, BRCA-mutated serous ovarian cancer, and a number of other cancers, including neuroblastoma, testicular and other germ cell tumors, Ewing's sarcoma, malignant lymphoma, breast cancer, colon cancer, and tyrosine kinase-activated leukemia.

Thus, PARP1 is a therapeutic target for a variety of serious conditions including various types of cancer and neurodegenerative diseases.

CDKs (cyclin-dependent kinases) are a family of enzymes that play an important role in the regulation of the cell cycle. Progression through the cell cycle is governed by a series of checkpoint controls, otherwise referred to as restriction points, which are regulated CDKs. In turn, the CDKs are regulated at many levels, for instance by binding to cyclins. Checkpoint controls are defective in tumor cells due, in part, to disregulation of CDK activity. For example, altered expression of Cyclin E and CDKs has been observed in tumor cells, and deletion of the CDK inhibitor p27 KIP gene in mice has been shown to result in a higher incidence of cancer, such as breast cancer.

Thus, both PARP1 and CDKs are involved various diseases, including cancer. Dual inhibitors of PARP1 and CDK of the present invention have not been heretofore disclosed.

SUMMARY

In various embodiments, the present disclosure provides for compounds that are dual inhibitors of PARP1 and CDK.

In some embodiments, the disclosure provides for compound having a structure according to Formula I,

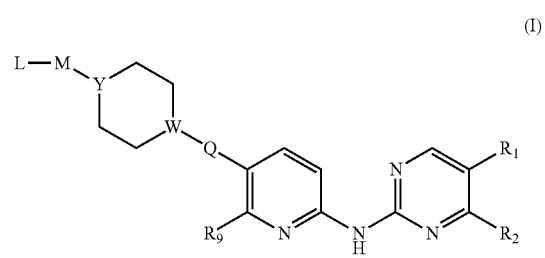

or a pharmaceutically acceptable salt, solvate, ester, or tautomer, thereof,
wherein:
M is a bond, —NH—, or —C(O)—;
L is a carbocyclyl, arylalkyl, heteroarylalkyl, or heterocyclyl, each of which is optionally substituted with one or more substituents;
Q is $CH_2$, O, S or a bond;
W and Y are independently CH or N, provided that at least one of W or Y is N, and when W is CH, Q is O or S; and
$R_1$ and $R_2$ are independently selected from hydrogen, halogen, alkyl, and heterocyclyl, each of which is optionally substituted with one or more substituents; or
$R_1$ and $R_2$ together with the atoms are to which they are attached form a carbocyclyl or heterocyclyl, each of which is optionally substituted with one or more substituents; and
$R_9$ is hydrogen, halogen, or alkyl, which is optionally substituted.

In some embodiments, W is N. In some embodiments, wherein Y is N. In some embodiments, each of W and Y are N. In some embodiments, $R_9$ is hydrogen.

In some embodiments, the compound of Formula (I) has a structure according to Formula (II):

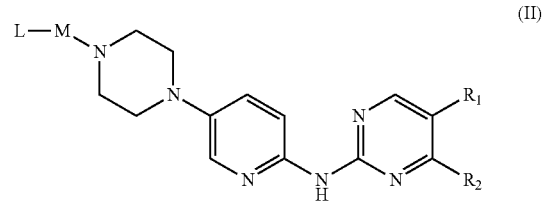

or a pharmaceutically acceptable salt, solvate, ester, or tautomer, thereof,
wherein:
M is a bond, —NH—, or —C(O)—;
L is a carbocyclyl, arylalkyl, heteroarylalkyl, or heterocyclyl, each of which is optionally substituted with one or more substituents;
$R_1$ and $R_2$ are independently selected from hydrogen, halogen, alkyl, and heterocyclyl, each of which is optionally substituted with one or more substituents; and
or $R_1$ and $R_2$ together with the atoms are to which they are attached form a carbocyclyl or heterocyclyl, each of which is optionally substituted with one or more substituents.

In some embodiments, L is substituted with one or more halogen, aryl, heteroaryl, arylalkyl, heteroarylalkyl, each of which is optionally substituted with one or more substituents. In some embodiments, each of the aryl, heteroaryl, arylalkyl, heteroarylalkyl are optionally substituted with one or more substituents selected from the group consisting of halogen, nitro, hydroxyl, ether, thiol, thioether, alkyl, aryl, heterocyclyl, —C(O), —C(O)NR$_g$R$_h$, wherein each of R$_g$ and R$_h$ are independently hydrogen or alkyl.

In some embodiments, L is (i) aryl which is optionally substituted with a halogen and a heteroarylalkyl which is optionally substituted with —C(O), (ii) arylalkyl which is optionally substituted with a heteroaryl which is optionally substituted with one or more halogen, —C(O), or combinations thereof, or (iii) aryl which is optionally substituted with a heteroaryl which is optionally substituted with —C(O)NR$_g$R$_h$, wherein each of R$_g$ and R$_h$ are independently hydrogen or alkyl. In some embodiments, L is a C$_{5-8}$ aryl which is optionally substituted with a halogen and a heteroarylalkyl comprising an 8-12-membered heteroaryl ring having from 1 to 4 atoms independently selected from nitrogen, oxygen and sulfur and which is optionally substituted with one or more substituents. In some embodiments, L is a C$_6$ aryl which is substituted with a halogen and a heteroarylalkyl comprising a 10-membered heteroaryl ring having 2 nitrogen atom and which is substituted with —C(O). In some embodiments, L is a C$_{5-8}$ aryl-C$_{1-3}$ alkyl which is optionally substituted with a 10-15-membered heteroaryl having from 1 to 4 atoms independently selected from nitrogen, oxygen and sulfur and which is optionally substituted with one or more halogen, —C(O), or combinations thereof. In some embodiments, L is C$_6$ aryl-C$_1$ alkyl which is substituted with 13-membered heteroaryl which having 2 nitrogen atoms and which is substituted with a halogen and —C(O). In some embodiments, L is a C$_{5-8}$ aryl which is optionally substituted a 6-12-membered heteroaryl having from 1 to 4 atoms independently selected from nitrogen, oxygen and sulfur and which is optionally substituted with —C(O)NR$_g$R$_h$, wherein each of R$_g$ and R$_h$ are independently hydrogen or alkyl. In some embodiments, L is a C$_6$ aryl which is substituted with a 9-membered heteroaryl having from 2 nitrogen atoms and is substituted with —C(O)NH$_2$.

In some embodiments, L is selected from the group consisting of:

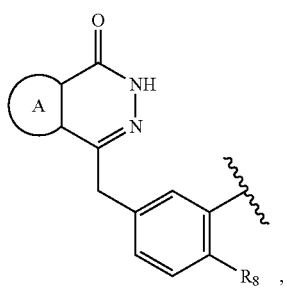

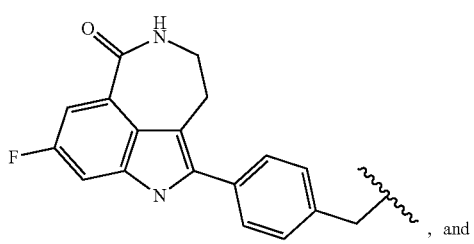
, and

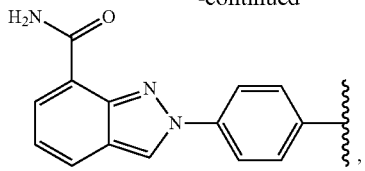

wherein:
the A ring represents a fused aryl or heteroaryl group, which is optionally substituted with one or more substituent groups selected from halogen, nitro, hydroxyl, ether, thiol, thioether, amino, alkyl, aryl and a heterocyclyl; and R$_8$ is hydrogen or halogen.

In some embodiments, L is

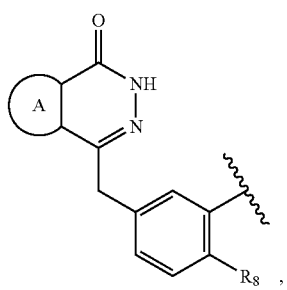

wherein:
the A ring represents a fused aryl or heteroaryl group, which is optionally substituted with one or more substituent groups selected from halogen, nitro, hydroxyl, ether, thiol, thioether, amino, alkyl, aryl and a heterocyclyl; and R$_8$ is hydrogen or halogen.

In some embodiments, the A ring is a C$_{5-8}$ aryl. In some embodiments, the A ring is benzene. In some embodiments, R$_8$ is selected from H, Cl, and F.

In some embodiments, R$_1$ is a halogen. In some embodiments, R$_2$ is a 6-12 membered heteroaryl which is optionally substituted with one or more substituents. In some embodiments, R$_2$ is 9-membered heteroaryl substituted with one or more substituents selected from halogen, alkyl, and combinations thereof.

In other embodiments, R$_2$ is

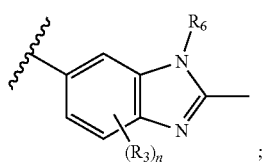
;

wherein
n is 0, 1, 2, or 3;
each R$_3$ is independently halogen or alkyl; and
R$_6$ is alkyl or cycloalkyl, each of which is optionally substituted with one or more substituents.

In some embodiments, n is 1. In some embodiments, $R_3$ is a $C_{1-3}$ alkyl. In some embodiments, $R_6$ is a $C_{1-3}$ alkyl. In still other embodiments, $R_2$ is selected from the group consisting of:

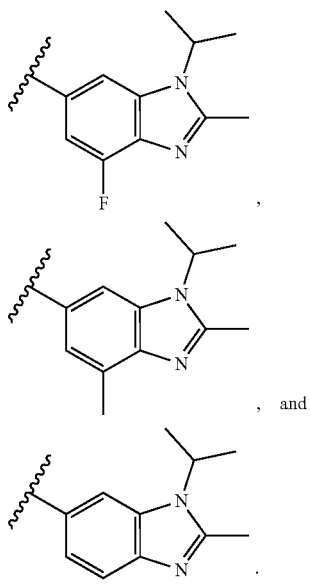

In some embodiments, $R_2$ is:

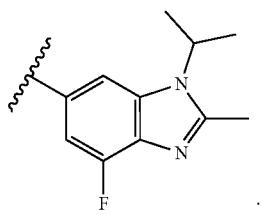 [SMILES: *c1cc(F)c2nc(C)n(C(C)C)c2c1]

In some embodiments, R1 and R2 together with the atoms to which they are attached form a heteroaryl which is optionally substituted with one or more substituents. In some embodiments, $R_1$ and $R_2$ together with the atoms are to which they are attached form a 5 to 6-membered heteroaryl which is substituted with one or more substituents selected from the group consisting of halogen, alkyl, cycloalkyl, and combinations thereof.

In other embodiments, $R_1$ and $R_2$ together with the atoms to which they are attached form a ring selected from the group consisting of:

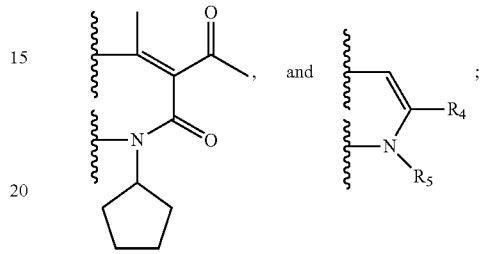

wherein:
$R_4$ is hydrogen or —C(O)NR$_a$R$_b$, wherein each of $R_a$ and $R_b$ are independently selected from hydrogen and alkyl; and
$R_5$ is cycloalkyl.

The compound of any one of claims 1-30, when $R_1$ and $R_2$ together with the atoms to which they are attached form

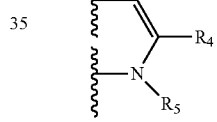

wherein $R_5$ is cyclopentyl, and $R_4$ is —C(O)N(CH$_3$)$_2$.
In some embodiments, $R_5$ is cyclopentyl, and each of $R_a$ and $R_b$ are both methyl.
In some embodiments, the compounds of the disclosure have the following structure:

C3

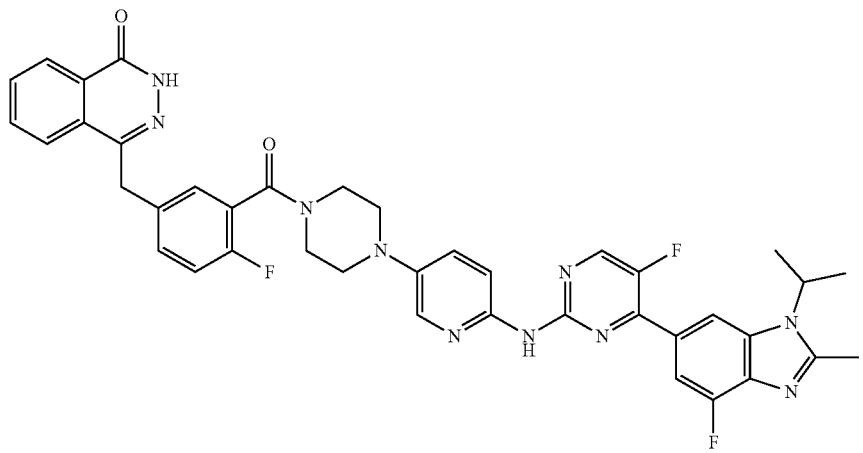

which is optionally substituted,
or a pharmaceutically acceptable salt, solvate, ester, or tautomer, thereof.

In some embodiments, the compounds of the disclosure have the following structure:

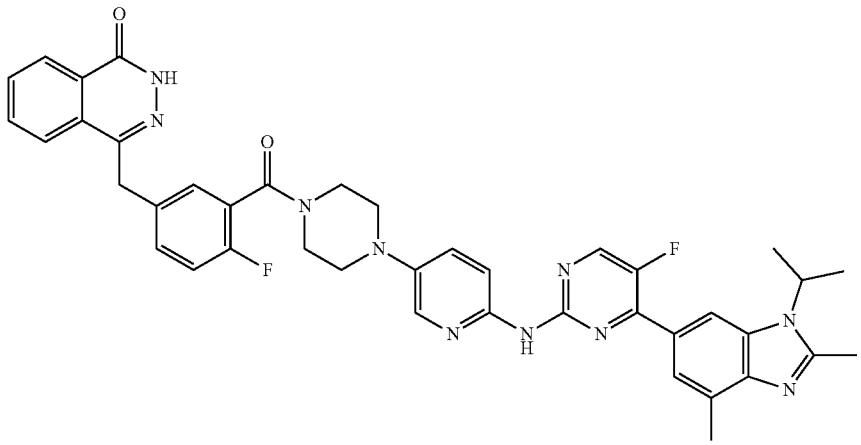 [SMILES: Cc1cc(-c2nc(Nc3ccc(N4CCN(C(=O)c5cc(Cc6n[nH]c(=O)c7ccccc67)ccc5F)CC4)cn3)ncc2F)cc2c1nc(C)n2C(C)C]

which is optionally substituted,
or a pharmaceutically acceptable salt, solvate, ester, or tautomer, thereof.

In some embodiments, the compounds of the disclosure have the following structure:

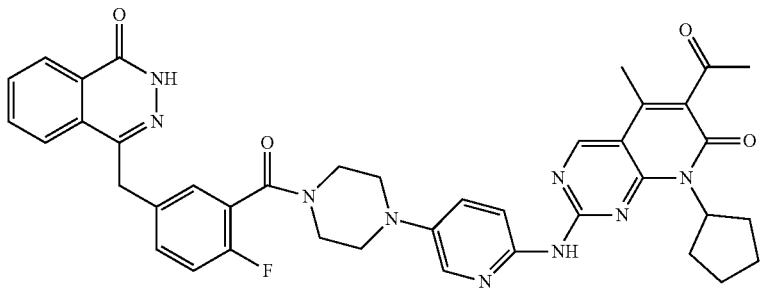 [SMILES: CC(=O)c1c(C)c2cnc(Nc3ccc(N4CCN(C(=O)c5cc(Cc6n[nH]c(=O)c7ccccc67)ccc5F)CC4)cn3)nc2n(C2CCCC2)c1=O]

which is optionally substituted,
or a pharmaceutically acceptable salt, solvate, ester, or tautomer, thereof.

In some embodiments, the compounds of the disclosure have the following structure:

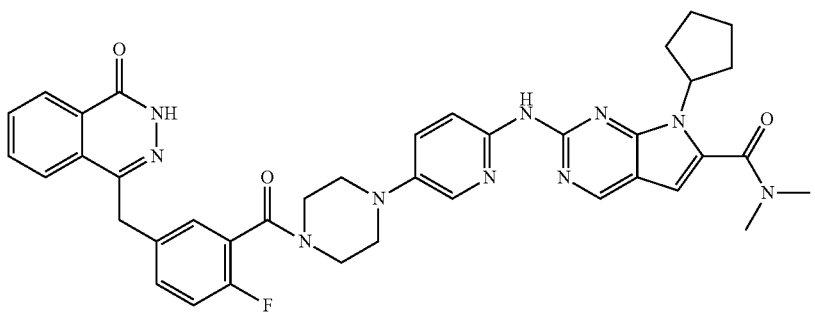 [SMILES: CN(C)C(=O)c1cc2cnc(Nc3ccc(N4CCN(C(=O)c5cc(Cc6n[nH]c(=O)c7ccccc67)ccc5F)CC4)cn3)nc2n1C1CCCC1]

which is optionally substituted,
or a pharmaceutically acceptable salt, solvate, ester, or tautomer, thereof.

In other embodiments, the present disclosure provides for pharmaceutical compositions comprising one or more compounds of Formula I, and at least one excipient. For example, in certain embodiments, the present disclosure provides for a pharmaceutical composition comprising a compound having the following structure:

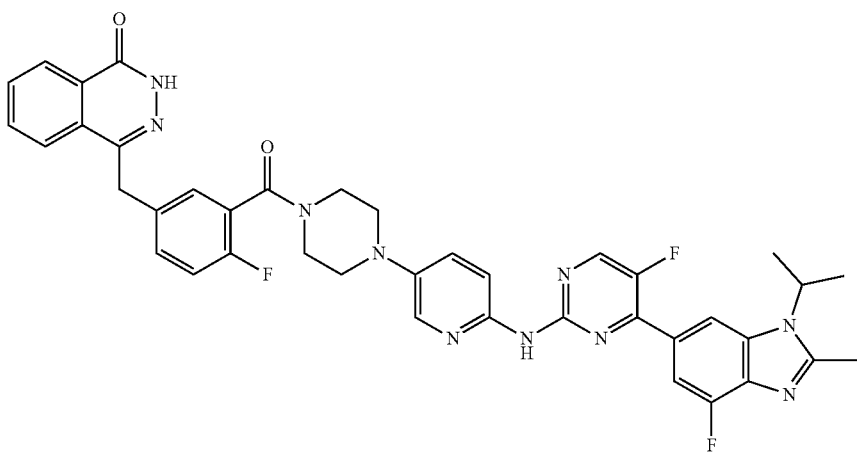

which is optionally substituted,
or a pharmaceutically acceptable salt, solvate, ester, or tautomer, thereof,
and at least one excipient.

In still other embodiments, the present disclosure provides or methods of treating a disease or condition in a patient in need thereof, comprising administering to the patient a therapeutically effective amount of one or more compounds of Formula I, thereby treating the disease or condition. For example, in certain embodiments, the present disclosure provides methods for treating a disease or condition in a patient in need thereof, comprising administering to that patient a therapeutically effective amount of a compound having the following structure:

which is optionally substituted,
or a pharmaceutically acceptable salt, solvate, ester, or tautomer, thereof,
thereby treating the patient.

In certain embodiments, the disease is cancer. In some embodiments, the cancer is colorectal cancer, breast cancer, lung cancer, especially non-small cell lung cancer (NSCLC), prostate cancer, glioblastoma, astrocytoma, mantel cell lymphoma (MCL), chronic myeloid leukemia (CML) and acute myeloid leukemia (AML), tyrosine kinase-activated leukemia, endometrial cancer, neuroblastoma, testicular cancer, germ cell tumors, Ewing's sarcoma, malignant lymphoma, recurrent epithelial ovarian cancer, fallopian tube cancer, or primary peritoneal cancer.

In other embodiments, the breast cancer is hormone receptor (HR)-positive breast cancer, and/or human epidermal growth factor receptor 2 (HER2)-negative advanced or metastatic breast cancer. In some embodiments, the breast cancer is hormone receptor (HR)-positive breast cancer, and the patient has disease progression following endocrine therapy and/or prior chemotherapy in metastatic setting.

In some embodiments, the breast cancer is human epidermal growth factor receptor 2 (HER2)-negative advanced or metastatic breast cancer, and the patient has disease

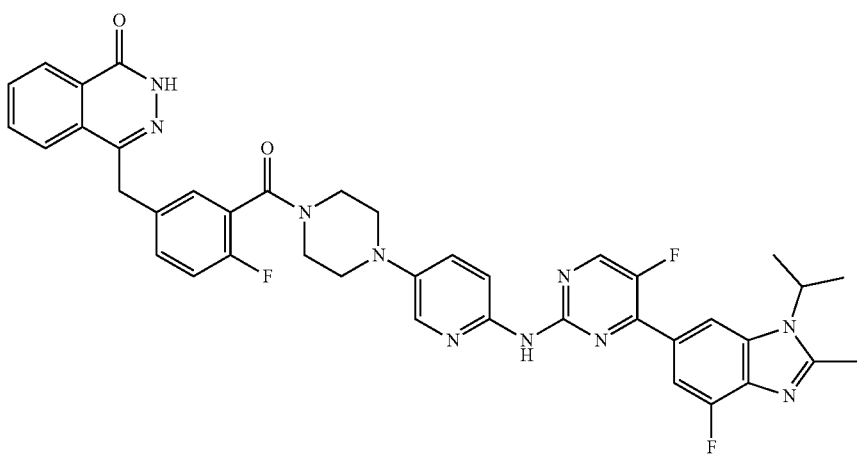

progression following endocrine therapy and/or prior chemotherapy in the metastatic setting. In other embodiments, the ovarian cancer is recurrent epithelial ovarian cancer. In some embodiments, the ovarian cancer is BRCA-mutated ovarian cancer. In some embodiments, the BRCA-mutated ovarian cancer is BRCA-mutated serous ovarian cancer. In some embodiments, the patient has suspected deleterious germline BRCA-mutated advanced ovarian cancer. In some embodiments, the patient has been treated with three or more prior lines of chemotherapy.

In yet still other embodiments, the cancer is triple negative breast cancer (TNBC). In even still other embodiments, the cancer is estrogen-receptor positive breast cancer.

In some embodiments, the disease or condition is vascular disease, septic shock, ischaemic injury, neurotoxicity, haemorraghic shock, viral infection, stroke, myocardial ischemia, diabetes, diabetes-associated cardiovascular dysfunction, traumatic central nervous system injury, arthritis, colitis, allergic encephalomyelitis, or inflammation.

DETAILED DESCRIPTION

Figure 1A:
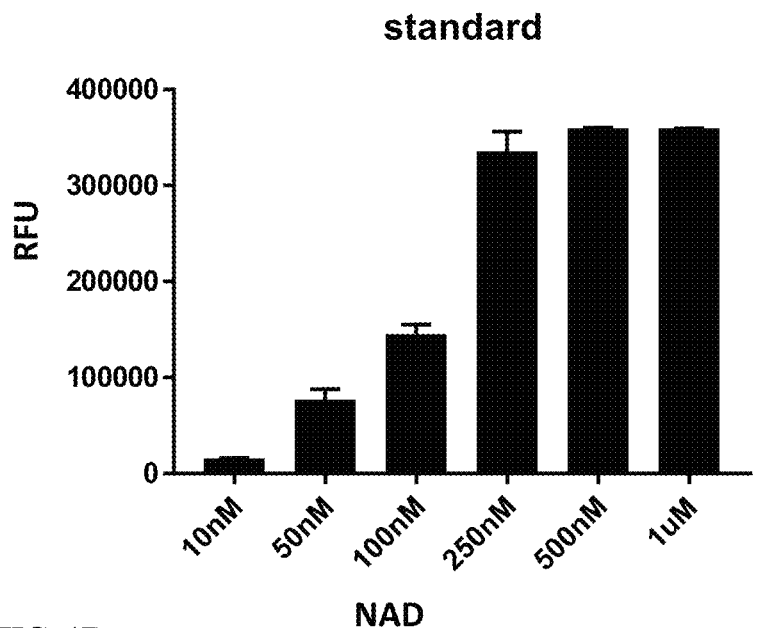
FIG. 1A graphically illustrates the relative fluorescence units (RFU) measured for increasing concentrations of nicotinamide adenine dinucleotide (NAD).

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

The term "a" or "an" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "pharmaceutically acceptable esters" include those obtained by replacing a hydrogen on an acidic group with an alkyl group, for example by reacting the acid group with an alcohol or a haloalkyl group. Examples of esters include, but are not limited to, replacing the hydrogen on an —C(O)OH group with an alkyl to form an —C(O)Oalkyl.

The term "pharmaceutically acceptable solvate" refers to a complex of solute (e.g., active compound, salt of active compound) and solvent. If the solvent is water, the solvate may be referred to as a hydrate, for example, a mono-hydrate, a di-hydrate, a tri-hydrate, etc.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the group through a single bond. The points of attachment of the alkylene chain to the rest of the molecule and to the group can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and Cm alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Aryl" refers to a hydrocarbon ring system comprising hydrogen, 6 to 18 carbon atoms and at least one aromatic ring, which is attached to the rest molecule by a single bond. For purposes of this invention, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the aryl can be optionally substituted.

"Aralkyl" or "arylalkyl" refers to a group of the formula —$R_b$—$R_c$ where $R_b$ is an alkylene group as defined above and $R_c$ is one or more aryls as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon consisting solely of carbon and hydrogen atoms, which can include fused or bridged ring systems, having from three to twenty carbon atoms, and which is attached to the rest of the molecule by a single bond. Monocyclic cycloalkyl include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl include, for example, cyclopentenyl, cyclohexenyl, cycloheptenyl, cyclooctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having from 3 to 20 carbon atoms and one or more carbon-carbon triple bonds, which can include fused or bridged ring systems, and which is attached to the rest of the molecule by a single bond. Monocyclic cycloalkynyls include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered aromatic or non-aromatic ring which consists of 2 to 12 carbon atoms and from one to six heteroatoms selected from the group consisting of nitrogen, oxygen and sulfur, and which is attached to the rest of the molecule by a single bond. Heterocyclycl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyls include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to thirteen carbon atoms, one to six heteroatoms selected from the group consisting of nitrogen, oxygen and sulfur, and at least one aromatic ring, and which is attached to the rest of the molecule by a single bond. For purposes of this disclosure, the heteroaryl can be a monocyclic, bicyclic, tricyclic or tetracyclic ring system, which can include fused or bridged ring systems; the heteroaryl may contain one or more non-aromatic rings (e.g., cycloalkyl or heterocyclyl) fused to the aromatic ring. The nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heteroarylalkyl" refers to a group of the formula —$R_b$—$R_f$ where $R_b$ is an alkylene chain as defined above and $R_f$ is a heteroaryl as defined above. Unless stated otherwise specifically in the specification, a heteroarylalkyl group can be optionally substituted.

The term "ether" used herein refers to a straight or branched divalent moiety —$[(CH_2)_m$—O—$(CH_2)_n]_z$— wherein each of m, n, and z are independently selected from 1 to 40. The term "thioether" used herein refers to a straight or branched divalent moiety —$[(CH_2)_m$—S—$(CH_2)_n]_z$— wherein each of m, n, and z are independently selected from 1 to 40.

The term "substituted" used herein means any of the above groups (i.e., alkyl, alkenyl, alkynyl, aryl, arylalkyl, carbocyclyl, cycloalkyl, cycloalkenyl, cycloalkynyl, heterocyclyl, N-heterocyclyl, heteroaryl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSO_2R_g$, $SO_2OR_g$, $=NSO_2R_g$, and $SO_2NR_gR_h$. "Substituted" also means any of the above groups in which one or more hydrogen atoms are replaced with $C(=O)R_g$, $C(=O)OR_g$, $C(=O)NR_gR_h$, $CH_2SO_2R_g$, $CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, "substituted" means any of the above groups in which two hydrogen atoms are each replaced by a bond to form a fused ring system containing the atoms to which the hydrogens were attached. Moreover, each of the foregoing substituents can also be optionally substituted with one or more of the above substituents.

The term "bond" is used herein to denote a direct coupling of the two adjacent groups, without any intervening atom or group. For example, when a group in Formula I is a bond, the group is effectively absent, and the moieties to which the group is depicted as being attached are bonded together.

The term "ring" may refer to a monocyclic, bicyclic, tricyclic or tetracyclic ring system, which can include fused or bridged ring systems.

Compounds

As discussed above, the present disclosure provides for compounds that are dual inhibitors of Parp1 and CDK. In some embodiments, the CDK is CDK 4 and/or CDK6.

As used herein, "inhibitors" refer to compounds which reduce the activity of both PARP1 and CDK. The reduction in activity of either enzyme can be by an amount in the range of from about 5% to about 100%, e.g., about 10%, about 15%, about 20%, about 25%, about 30%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%, inclusive of all values and subranges therebetween. In other embodiments, the compounds disclosed herein can reduce the activity of either enzyme by at least about 5%, at least about 10%, at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%.

In some embodiments, the compounds of the disclosure can reduce the total activity of both Parp1 and CDK by an amount in the range of from about 5% to about 100%, e.g., about 10%, about 15%, about 20%, about 25%, about 30%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%, inclusive of all values and subranges therebetween. In other embodiments, the compounds disclosed herein can be reduce the total activity of both Parp1 and CDK by at least about 5%, at least about 10%, at least about 15%, at least about 20%, at least about 25%, at least about 30%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100%.

In various embodiments, the present disclosure provides for a compound having a structure according to Formula I,

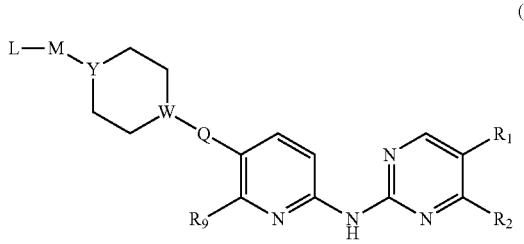

(I)

or a pharmaceutically acceptable salt, solvate, ester, or tautomer, thereof,

In some embodiments, M is a bond, —NH—, or —C(O)—.

In some embodiments, L is a carbocyclyl, arylalkyl, heteroarylalkyl, or heterocyclyl, each of which is optionally substituted with one or more substituents.

In some embodiments, Q is $CH_2$, O, S or a bond.

In some embodiments, W and Y are independently CH or N. In other embodiments, at least one of W or Y is N. In still other embodiments, when W is CH, Q is O or S.

In some embodiments, $R_1$ and $R_2$ are independently selected from hydrogen, halogen, alkyl, and heterocyclyl, each of which is optionally substituted with one or more substituents. In alternative embodiments, $R_1$ and $R_2$ together with the atoms are to which they are attached form a carbocyclyl or heterocyclyl, each of which is optionally substituted with one or more substituents; and In some embodiments, $R_9$ is hydrogen, halogen, or alkyl. In certain embodiments, the alkyl is a $C_{1-7}$ alkyl. In particular embodiments, the alkyl (e.g., the $C_{1-7}$ alkyl) is —$CH_3$.

In some embodiments, Q is a bond. In some embodiments, W is N. In some embodiments, Y is N. In some embodiments, $R_9$ is alkyl. In particular embodiments, Q is a bond, W and Y are N, and $R_9$ is alkyl. In some embodiments, $R_9$ is hydrogen.

In some embodiments, the compounds of Formula I have a structure according to Formula II,

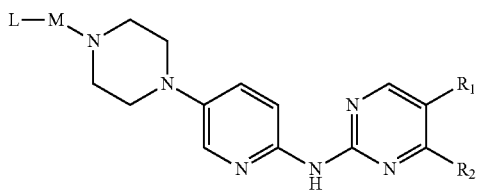

(II)

or a pharmaceutically acceptable salt, solvate, ester, or tautomer, thereof, and M, L, $R_1$ and $R_2$ are defined above.

In some embodiments, M is a bond. In some embodiments, M is —NH—. In some embodiments, M is —C(O)—.

In some embodiments, L is carbocyclyl, arylalkyl, heteroarylalkyl, or heterocyclyl, each of which is optionally substituted with one or more substituents described herein. In some embodiments, L is carbocyclyl, arylalkyl, or heterocyclyl, each of which is optionally substituted with one or more substituents described herein. In some embodiments, the substituents may include halogen, aryl, heteroaryl, arylalkyl, heteroarylalkyl, each of which is optionally substituted with one or more substituents described herein. In some embodiments, the substituents are selected from the group consisting of halogen, nitro, hydroxyl, ether, thiol, thioether, alkyl, aryl, heterocyclyl, —C(O), —C(O)$NR_gR_h$, wherein each of $R_g$ and $R_h$ are independently hydrogen or alkyl In some embodiments, the carbocyclyl is a $C_{5-8}$ aryl which is optionally substituted with halogen and a heteroarylalkyl comprising an 8-12-membered heteroaryl ring having from 1 to 4 atoms independently selected from nitrogen, oxygen and sulfur and which is optionally substituted with one or more substituents described herein. In particular embodiments, the carbocyclyl is a $C_6$ aryl, which is substituted with a halogen (e.g., —F) and a heteroarylalkyl comprising a 10-membered ring having 2 nitrogen atoms and which is substituted with —C(O). In some embodiments, the arylalkyl is $C_{5-8}$ aryl-$C_{1-3}$ alkyl which is optionally substituted with a 10-15-membered heteroaryl having from 1 to 4 atoms independently selected from nitrogen, oxygen and sulfur and which is optionally substituted with one or more substituents described herein. In some embodiments, the arylalkyl is a $C_6$ aryl-$C_1$ alkyl which is substituted with 13-membered heteroaryl which having 2 nitrogen atoms and which is substituted with one or more halogen, —C(O), and combinations thereof. In some embodiments, the carbocyclyl is a $C_{5-8}$ aryl which is optionally substituted with a 6-12-membered heteroaryl having from 1 to 4 atoms independently selected from nitrogen, oxygen and sulfur and which is optionally substituted with one or more substituents described herein. In some embodiments, the carbocyclyl is a $C_6$ aryl which is substituted with a 9-membered heteroaryl having from 2 nitrogen atoms and is substituted with —C(O)$NR_gR_h$, wherein each of $R_g$ and $R_h$ are independently hydrogen or alkyl.

In some embodiments, L is selected from the group consisting of:

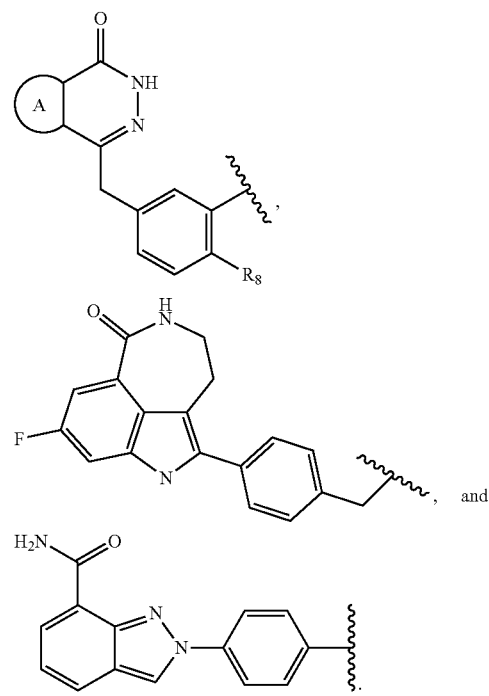

In particular embodiments, L is

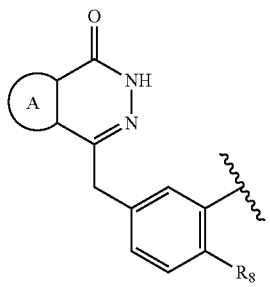

In some embodiments, the A ring represents a fused aryl or heteroaryl group, which is optionally substituted with one or more substituent groups selected from halogen, nitro, hydroxyl, ether, thiol, thioether, amino, alkyl, aryl and a heterocyclyl. In some embodiments, the fused aryl group is benzene. In some embodiments, the alkyl is a $C_{1-7}$ alkyl. In some embodiments, the aryl is a $C_{5-20}$ aryl. In some embodiments, the heterocyclyl is a 3 to 7 membered heterocyclyl having from 1 to 4 atoms independently selected from nitrogen, oxygen and sulfur. In some embodiments, $R_8$ is hydrogen or halogen. In some embodiments, $R_8$ is selected from —H, —Cl, and —F.

In some embodiments, L is

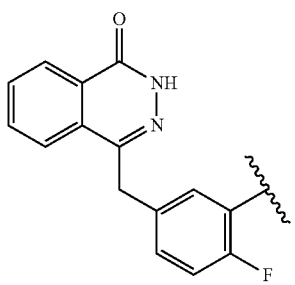 [SMILES: *c1cc(Cc2n[nH]c(=O)c3ccccc23)ccc1F]

In some embodiments, $R_1$ and $R_2$ are independently selected from hydrogen, halogen, alkyl, carbocyclyl, or heterocyclyl, each of which is optionally substituted with one or more substituents. 4. In some embodiments, $R_2$ is a 6-15 membered heteroaryl having from 1 to 4 atoms independently selected from nitrogen, oxygen, and sulfur, and substituted with one or more substituents selected from halogen, alkyl, and combinations thereof. In some embodiments, $R_2$ is a 9-membered heteroaryl having two nitrogen atoms and which is substituted with one or more substituents selected from halogen, alkyl, and combinations thereof. In other embodiments, $R_2$ is

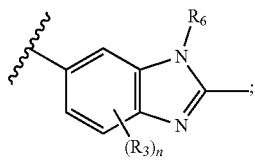

wherein n is 0, 1, 2, or 3; each $R_3$ is independently selected from halogen, or alkyl; and $R_6$ is alkyl or cycloalkyl, each of which is optionally substituted. In some embodiments, the alkyl is a $C_{3-5}$ alkyl. In other embodiments, the cycloalkyl is a $C_{3-5}$ cycloalkyl. In some embodiments, $C_{3-5}$ cycloalkyl is a cyclopropryl which is optionally substituted with an alkyl group. In certain embodiments, $R_6$ is selected from the group consisting of isopropyl, cyclopropyl, cyclopentyl or cyclopropyl-methyl. In some embodiments, $R_2$ is

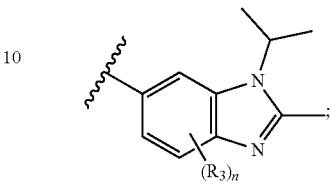

wherein n is 0, 1, 2, or 3; and each $R_3$ is independently selected from halogen or alkyl. In further embodiments, $R_2$ is selected from the group consisting of:

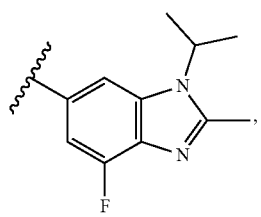

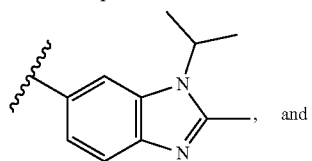, and

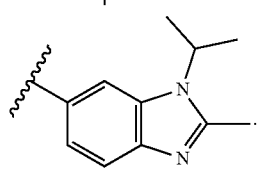

In particular embodiments, $R_2$ is:

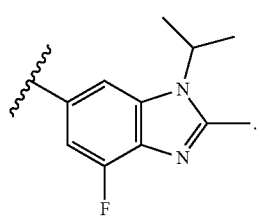 [SMILES: *c1cc(F)c2nc(C)n(C(C)C)c2c1]

In alternative embodiments, $R_1$ and $R_2$ together with the atoms are to which they are attached form a heterocyclyl, which is optionally substituted with one or more substituents. In some embodiments, $R_1$ and $R_2$ together with the atoms are to which they are attached form a 5 to 6-membered heteroaryl which is substituted with one or more substituents selected from the group consisting of halogen, alkyl, cycloalkyl, and combinations thereof. In some embodiments, $R_1$ and $R_2$ together with the atoms to which they are attached form a ring selected from the group consisting of:

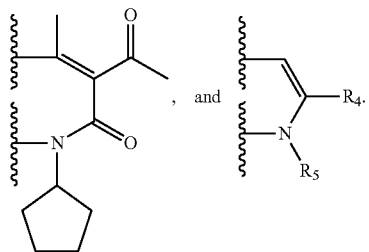

In some embodiments, $R_4$ is hydrogen or $C(O)NR_aR_b$, wherein each of $R_a$ and $R_b$ are independently selected from an alkyl. In some embodiments, the alkyl is a $C_{1-8}$ alkyl. In some embodiments, $R_5$ is cycloalkyl. In other embodiments, the cycloalkyl is a $C_{3-14}$ cycloalkyl. In particular embodiments, $R_5$ is cyclopentyl, and each of $R_a$ and $R_b$, when present, are methyl.

In certain embodiments, $R_1$ and $R_2$ together with the atoms to which they are attached form the following ring:

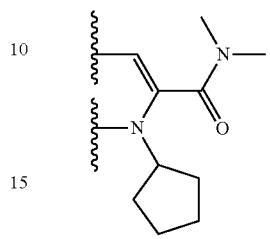

In some embodiments, the compounds of the present disclosure are selected from Table 1.

TABLE 1

| Compound No. | Structure |
| --- | --- |
| C3 | 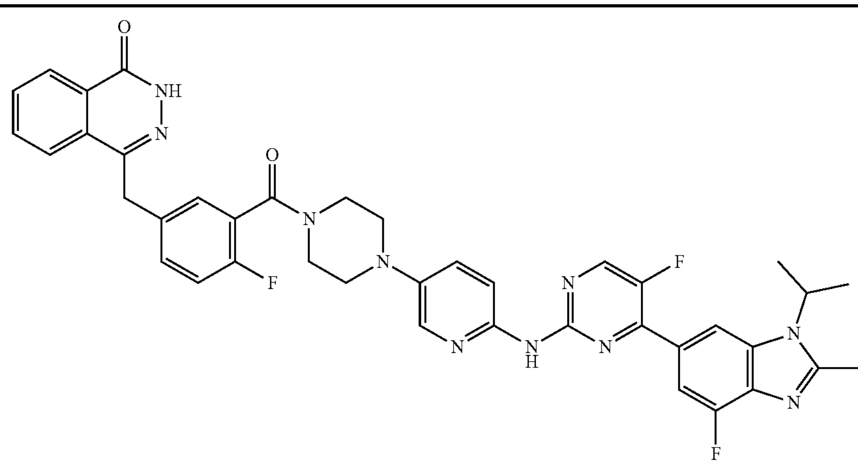 |
| C3-1 | 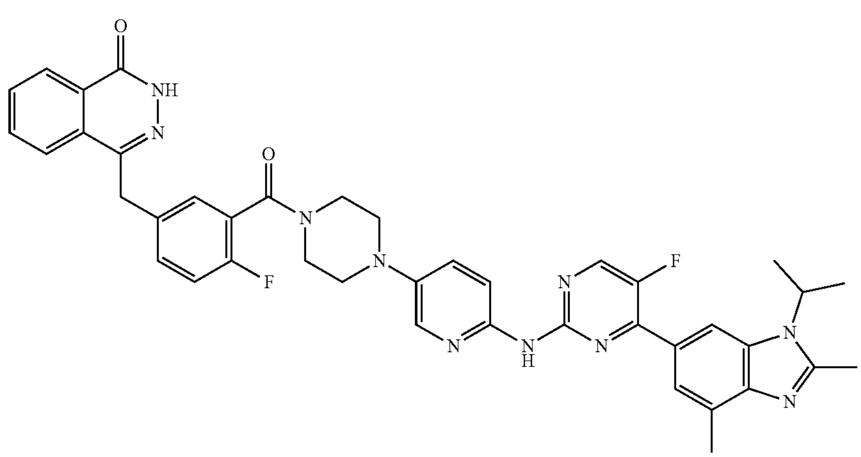 [SMILES: Cc1cc(-c2nc(Nc3ccc(N4CCN(C(=O)c5cc(Cc6n[nH]c(=O)c7ccccc67)ccc5F)CC4)cn3)ncc2F)cc2c1nc(C)n2C(C)C] |

TABLE 1-continued

| Compound No. | Structure |
|---|---|
| C3-2 | 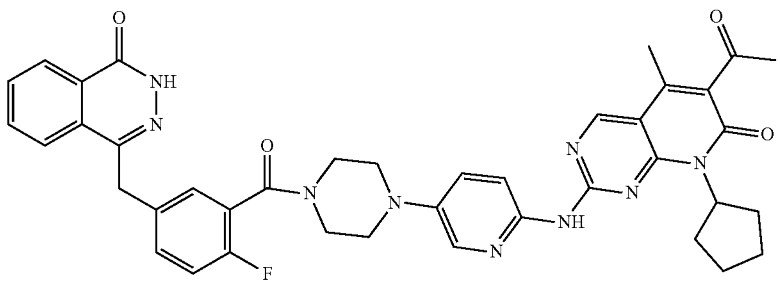 [SMILES: CC(=O)c1c(C)c2cnc(Nc3ccc(N4CCN(C(=O)c5cc(Cc6n[nH]c(=O)c7ccccc67)ccc5F)CC4)cn3)nc2n(C2CCCC2)c1=O] |
| C3-3 | 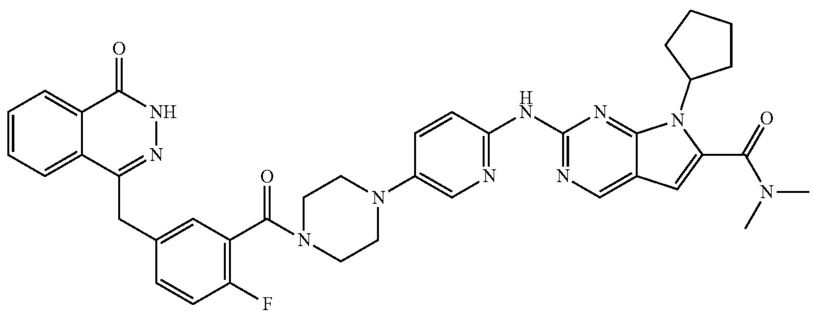 [SMILES: CN(C)C(=O)c1cc2cnc(Nc3ccc(N4CCN(C(=O)c5cc(Cc6n[nH]c(=O)c7ccccc67)ccc5F)CC4)cn3)nc2n1C1CCCC1] |
| C3-4 | 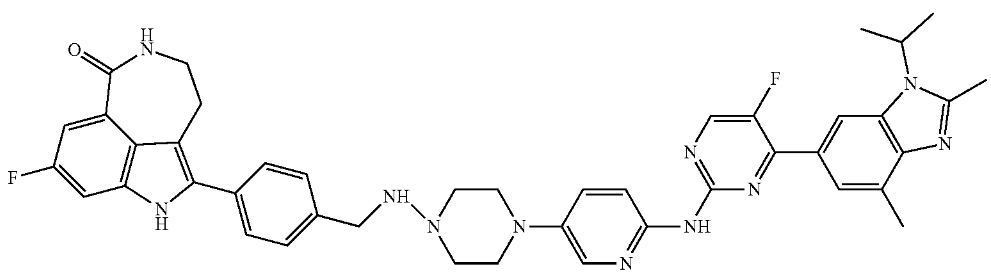 [SMILES: Cc1cc(-c2nc(Nc3ccc(N4CCN(NCc5ccc(-c6[nH]c7cc(F)cc8c7c6CCNC8=O)cc5)CC4)cn3)ncc2F)cc2c1nc(C)n2C(C)C] |
| C3-5 | 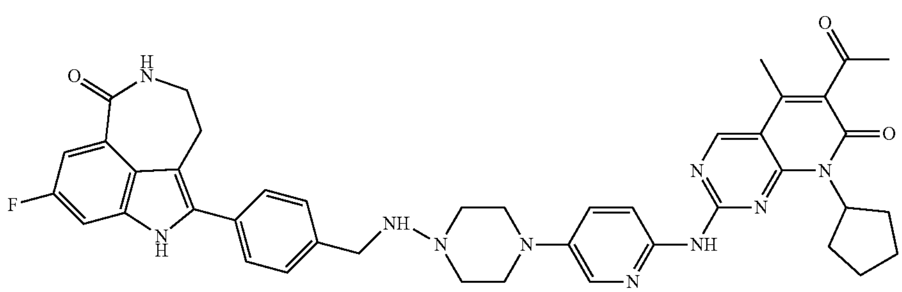 [SMILES: CC(=O)c1c(C)c2cnc(Nc3ccc(N4CCN(NCc5ccc(-c6[nH]c7cc(F)cc8c7c6CCNC8=O)cc5)CC4)cn3)nc2n(C2CCCC2)c1=O] |
| C3-6 | 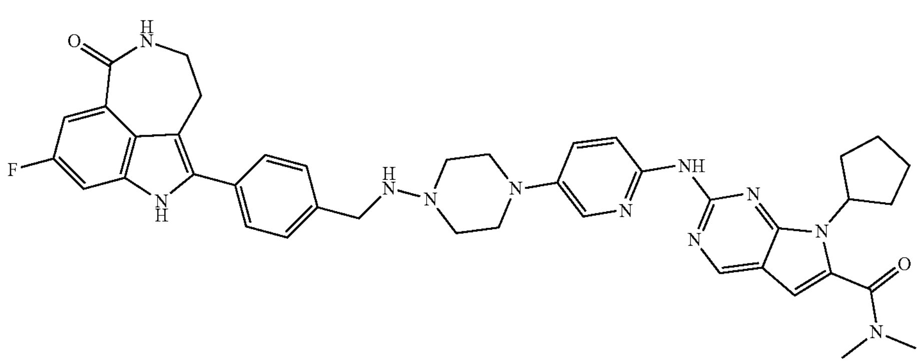 [SMILES: CN(C)C(=O)c1cc2cnc(Nc3ccc(N4CCN(NCc5ccc(-c6[nH]c7cc(F)cc8c7c6CCNC8=O)cc5)CC4)cn3)nc2n1C1CCCC1] |

TABLE 1-continued
| Compound No. | Structure |
|---|---|
| C3-7 | 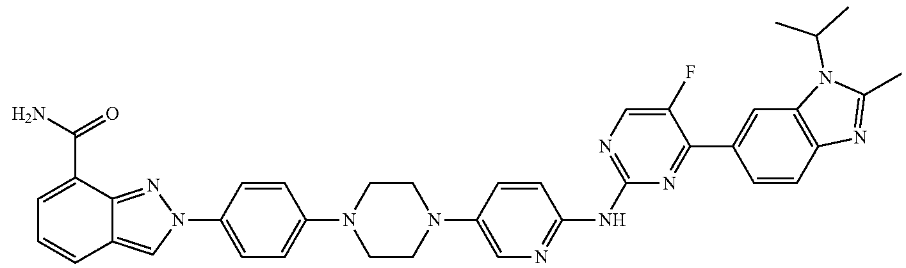 [SMILES: Cc1nc2ccc(-c3nc(Nc4ccc(N5CCN(c6ccc(-n7cc8cccc(C(N)=O)c8n7)cc6)CC5)cn4)ncc3F)cc2n1C(C)C] |
| C3-8 | 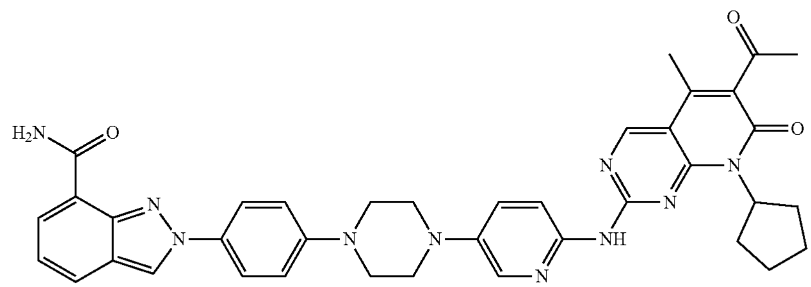 [SMILES: CC(=O)c1c(C)c2cnc(Nc3ccc(N4CCN(c5ccc(-n6cc7cccc(C(N)=O)c7n6)cc5)CC4)cn3)nc2n(C2CCCC2)c1=O] |
| C3-9 | 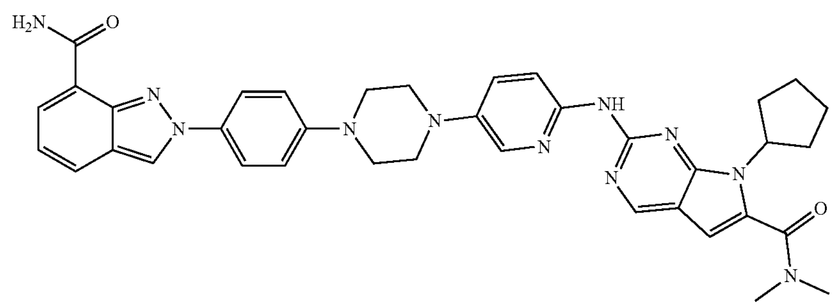 [SMILES: CN(C)C(=O)c1cc2cnc(Nc3ccc(N4CCN(c5ccc(-n6cc7cccc(C(N)=O)c7n6)cc5)CC4)cn3)nc2n1C1CCCC1] |
In some embodiments, the compounds disclosed herein have the following structure:
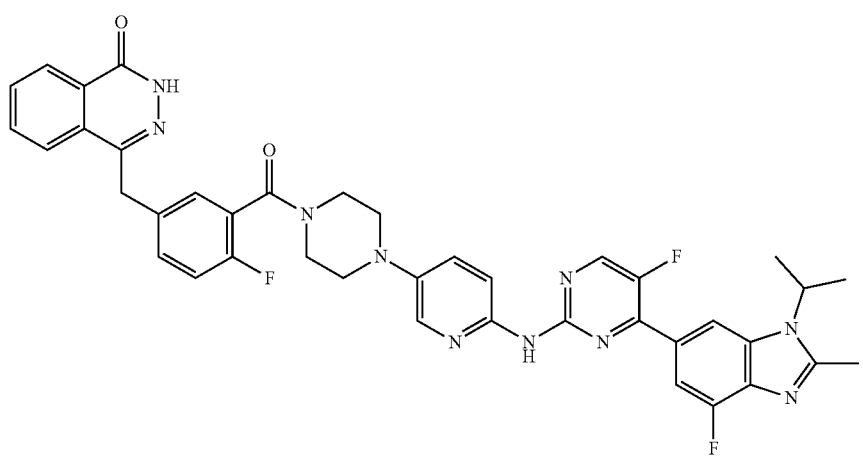
C3

In some embodiments, C3 is optionally substituted. In some embodiments, the compounds of disclosure include one or more pharmaceutically acceptable salts, solvates, esters, or tautomers of (optionally substituted) C3.

Pharmaceutical Compositions

The present disclosure also includes pharmaceutical compositions comprising one or more dual inhibitors of PARP1 and CDK. In some embodiments, pharmaceutical compositions comprise one or more compounds of Formula I, or pharmaceutically acceptable salts, solvates, esters, or tautomers. In other embodiments, pharmaceutical compositions comprise one or more compounds selected from Table 1, or pharmaceutically acceptable salts, solvates, esters, or tautomers. In particular embodiments, the pharmaceutical composition comprises a compound having the following structure:

viral infection, stroke, myocardial ischemia, diabetes, diabetes-associated cardiovascular dysfunction, traumatic central nervous system injury, arthritis, colitis, allergic encephalomyelitis, or inflammation. In a particular embodiment, the additional therapeutic agent is fluvestrant or platinum-based chemotherapy.

As discussed above, in some embodiments, pharmaceutical compositions described herein can be combined with one or more therapeutically active agents used in the treatment of cancer. The additional therapeutic agent can be administering subsequently, simultaneously, or sequentially (e.g., before or after) with respect to the dual PARP1 and CDK inhibitor. Non-limiting examples of additional therapeutic agents that can be combined with the methods disclosed herein include: fluvestrant, temozolomide, gemcitabine, letrozole, chemotherapy, and radiation therapy.

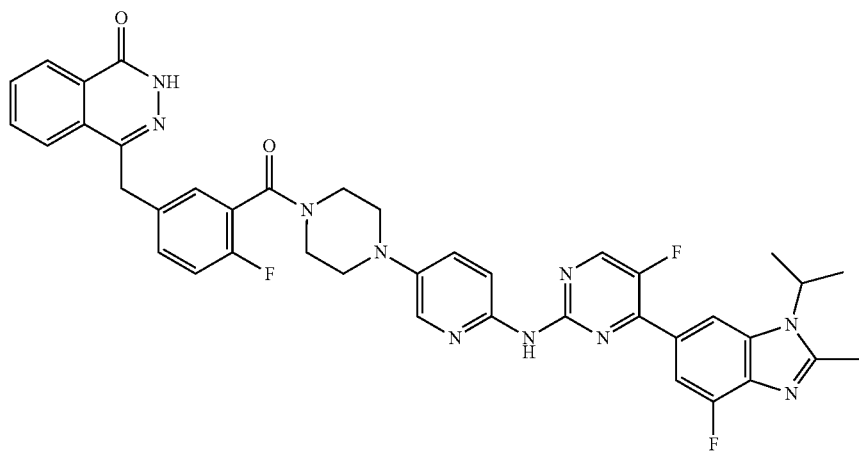

C3

In some embodiments, pharmaceutical compositions comprise a therapeutically effective amount of one or more compounds of Formula I, or pharmaceutically acceptable salts, solvates, esters, or tautomers. In other embodiments, pharmaceutical compositions comprise a therapeutically effective amount of one or more compounds selected from Table 1, or pharmaceutically acceptable salts, solvates, esters, or tautomers. In particular embodiments of the present disclosure, pharmaceutical compositions comprise a therapeutically effective amount of one or more of C3, and pharmaceutically acceptable salts, solvates, esters, or tautomers thereof.

In some embodiments, the pharmaceutical compositions, as described herein, comprising one or more compounds of Formula I, and pharmaceutically acceptable salts, solvates, esters, or tautomers thereof, further comprises one or more additional therapeutically active agents. In other embodiments, the pharmaceutical compositions comprising one or more compounds of Table 1, and pharmaceutically acceptable salts, solvates, esters, or tautomers thereof, further comprises one or more additional therapeutically active agents. In particular embodiments, the pharmaceutical compositions comprising one or more compounds of C3 and pharmaceutically acceptable salts, solvates, esters, or tautomers thereof, further comprises one or more additional therapeutically active agents. In one embodiment, one or more additional therapeutically active agents are selected from therapeutics useful for cancer, vascular disease, septic shock, ischaemic injury, neurotoxicity, haemorraghic shock, In further embodiments of the present disclosure, pharmaceutical compositions comprising one or more compounds of Formula I (including compounds in Table 1, and in particular C3), or a pharmaceutically acceptable salt, solvate, ester, or tautomer, thereof, and a pharmaceutically acceptable excipient or adjuvant is provided. The pharmaceutically acceptable excipients and adjuvants are added to the composition or formulation for a variety of purposes. In other embodiments, a pharmaceutical compositions comprising one or more compounds of Formula I (including compounds in Table 1, and in particular C3), or a pharmaceutically acceptable salt, solvate, ester, or tautomer, thereof, further comprise a pharmaceutically acceptable carrier. In some embodiments, a pharmaceutically acceptable carrier includes a pharmaceutically acceptable excipient, binder, and/or diluent. In some embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In some embodiments, the present disclosure provides pharmaceutical compositions comprising one or more compounds of Formula I (including compounds in Table 1, and in particular C3), or a pharmaceutically acceptable salt, solvate, ester, or tautomer, thereof, combined with a pharmaceutically acceptable carrier. In some embodiments, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M phosphate buffer or saline (e.g., about 0.8%). Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microtine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

In various embodiments, the pharmaceutical composition may be selected from the group consisting of a solid, powder, liquid and a gel. In certain embodiments, the pharmaceutical compositions of the present disclosure is a solid (e.g., a powder, tablet, a capsule, granulates, and/or aggregates). In certain of such embodiments, the solid pharmaceutical composition comprises one or more excipients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of Formula I (including compounds in Table 1, and in particular C3), or a pharmaceutically acceptable salt, solvate, ester, or tautomer, thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical compositions of the present invention are formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of one or more of Formula I (including compounds in Table 1, and in particular C3), or a pharmaceutically acceptable salt, solvate, ester, or tautomer thereof, (or composition comprising such) to achieve a desired biological response, e.g., an amount effective to alleviate, ameliorate, or prevent, in whole or in part, a symptom of a condition to be treated. In various embodiments, the route of administration is systemic, e.g., oral or by injection.

In certain embodiments, the pharmaceutical compositions of the present disclosure are prepared for oral administration. In certain of such embodiments, the pharmaceutical compositions are formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, the pharmaceutical compositions for oral administration are soft, sealed capsules made of gelatin and a plasticizer, such as glycerol or sorbitol. In certain soft capsules, one or more of Formula I (including compounds in Table 1, and in particular C3), or a pharmaceutically acceptable salt, solvate, ester, or tautomer thereof, are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, one or more compounds of Formula I (including compounds in Table 1, and in particular C3), or a pharmaceutically acceptable salt, solvate, ester, or tautomer thereof, are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of compounds of Formula I (including compounds in Table 1, and in particular C3), or a pharmaceutically acceptable salt, solvate, ester, or tautomer thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be once administered daily or more frequently depending upon a number of factors, including the overall health of a patient, and the formulation and route of administration of the selected compound(s).

The compounds or pharmaceutical compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

Methods of Treatment

The present disclosure also includes methods for inhibiting PARP1 and CDK in a subject. In some embodiments, the methods comprise administering one or more compounds of Formula I (including compounds in Table 1, and in particular C3), and pharmaceutically acceptable salts, solvates, esters, or tautomers thereof. In some embodiments, one or more compounds of Formula I (including compounds in Table 1, and in particular C3), and a pharmaceutically acceptable salts, solvates, esters, or tautomers thereof, in a pharmaceutical composition as described herein, treats a patient suffering from cancer, vascular disease, septic shock, ischaemic injury, neurotoxicity, haemorraghic shock, viral infection, stroke, myocardial ischemia, diabetes, diabetes-associated cardiovascular dysfunction, traumatic central nervous system injury, arthritis, colitis, allergic encephalomyelitis, or inflammation.

In some embodiments, the cancer is colorectal cancer, breast cancer, lung cancer, especially non-small cell lung cancer (NSCLC) prostate cancer, glioblastoma, mantel cell lymphoma (MCL), chronic myeloid leukemia (CML) and acute myeloid leukemia (AML), tyrosine kinase-activated leukemia, endometrial cancer, neuroblastoma, testicular cancer, germ cell tumors, Ewing's sarcoma, malignant lymphoma, ovarian cancer, fallopian tube cancer, or primary peritoneal cancer.

In other embodiments, the breast cancer is hormone receptor (HR)-positive breast cancer, and/or human epidermal growth factor receptor 2 (HER2)-negative advanced or metastatic breast cancer. In some embodiments, the breast cancer is hormone receptor (HR)-positive breast cancer, and the patient has disease progression following endocrine therapy and/or prior chemotherapy in metastatic setting.

In some embodiments, the breast cancer is human epidermal growth factor receptor 2 (HER2)-negative advanced or metastatic breast cancer, and the patient has disease progression following endocrine therapy and/or prior chemotherapy in the metastatic setting. In other embodiments, the ovarian cancer is recurrent epithelial ovarian cancer. In some embodiments, the ovarian cancer is BRCA-mutated ovarian cancer. In some embodiments, the BRCA-mutated ovarian cancer is BRCA-mutated serous ovarian cancer. In some embodiments, the patient has suspected deleterious germline BRCA-mutated advanced ovarian cancer. In some embodiments, the patient has been treated with three or more prior lines of chemotherapy.

In some embodiments, the cancer is triple negative breast cancers (TNBC), which are characterized by breast cancer cells that test negative for estrogen receptors (ER-), progesterone receptors (PR-), and HER2 (HER2-). Testing negative for all three of these means the cancer is triple-negative. In some embodiments, the cancer is estrogen-receptor positive breast cancer.

In another embodiment the cancer may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Non-melanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

In some embodiments of the present disclosure, pharmaceutical compositions comprise a therapeutically effective amount of one or more of compounds of Formula I (including compounds in Table 1, and in particular C3), and a pharmaceutically acceptable salts, solvates, esters, or tautomer thereof.

In some embodiments, the pharmaceutical compositions, as described herein, comprising one or more of compounds of Formula I (including compounds in Table 1, and in particular C3), and a pharmaceutically acceptable salts, solvates, esters, or tautomers thereof, further comprises one or more additional therapeutically active agents. In one embodiment, one or more additional therapeutically active agents are selected from therapeutics useful for treating cancer, vascular disease, septic shock, ischaemic injury, neurotoxicity, haemorraghic shock, viral infection, stroke, myocardial ischemia, diabetes, diabetes-associated cardiovascular dysfunction, traumatic central nervous system injury, arthritis, colitis, allergic encephalomyelitis, or inflammation.

The methods of the present disclosure can be combined with other therapies used in the treatment of the above indications. In some embodiments, such combination therapies entail administering an additional therapeutic agent. The additional therapeutic agent can be administering subsequently, simultaneously, or sequentially (e.g., before or after) with respect to the dual Parp1 and CDK inhibitor. Non-limiting examples of additional therapeutic agent which can be combined with the methods disclosed herein include: letrazole, olaparib, palbocicilib, and abemaciclib.

Incorporation by Reference

The following patents are incorporated by reference in their entirety for all purposes: U.S. Pat. Nos. 7,151,102; 7,449,464; 7,981,889; 8,143,241; 8,247,416; 8,475,842; 8,859,562; 8,912,187; and 7,855,211

SYNTHETIC EXAMPLES

Synthetic Example 1

The compounds described herein can be prepared using synthetic techniques known to one skilled in the art of organic synthesis or variations thereon as appreciated by those skilled in the art. Synthetic techniques can be found, for example, in Cary and Sundberg, Advanced Organich Chemistry, Part B: Reactions and Synthesis, $5^{th}$ Ed. Springer, 2007, and Corey and Cheng, The Logic of Chemical Synthesis, $4^{th}$ Ed., Wiley and Sons, 1995, U.S. Pat. Nos. 7,855,211 and 7,449,464 each of which is herein incorporated by reference in its entirety. The compounds described herein can be prepared from readily available starting materials. Optimum reaction conditions can vary with the particular reactants or solvents used, but such conditions can be determined by one skilled in the art.

When one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

General Synthetic Scheme

Compounds of formula I may be synthesized according to the following general scheme, where any groups not specifically defined in the scheme have the definition provided herein:

Step 1: Palladium-Catalyzed Coupling of a Substituted Pyrimidinyl to Pyridinyl Amine

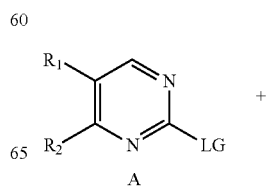

A

43

-continued

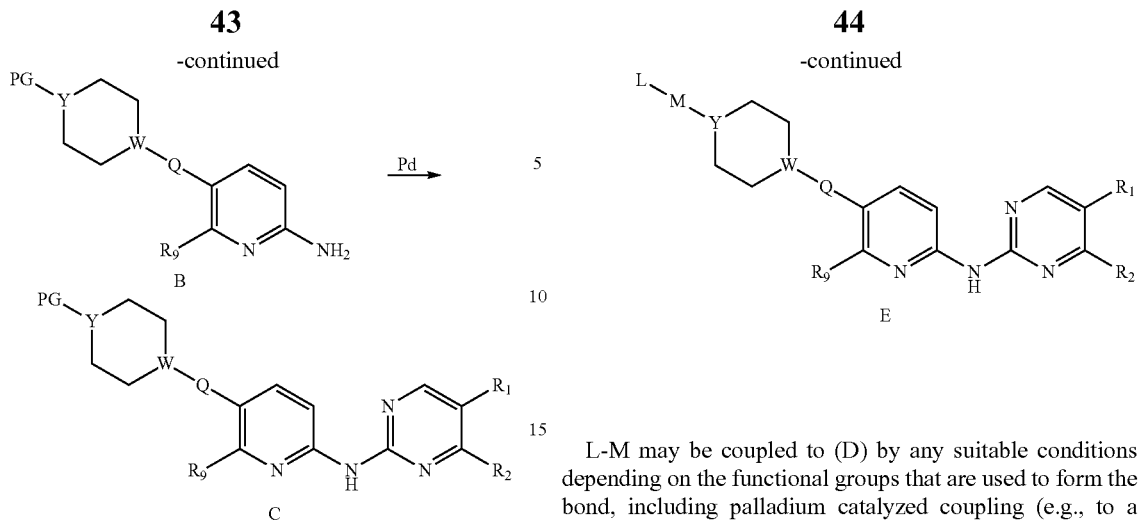

In the above scheme, LG is an appropriate leaving group, such as chloride, and PG is an appropriate protecting group. The substituted pyrimidinyl-chloride (A) is reacted with a pyridinyl amine (B) in a palladium catalyzed coupling reaction to form protected precursor compounds (C) of formula I.

Step 2: Deprotection

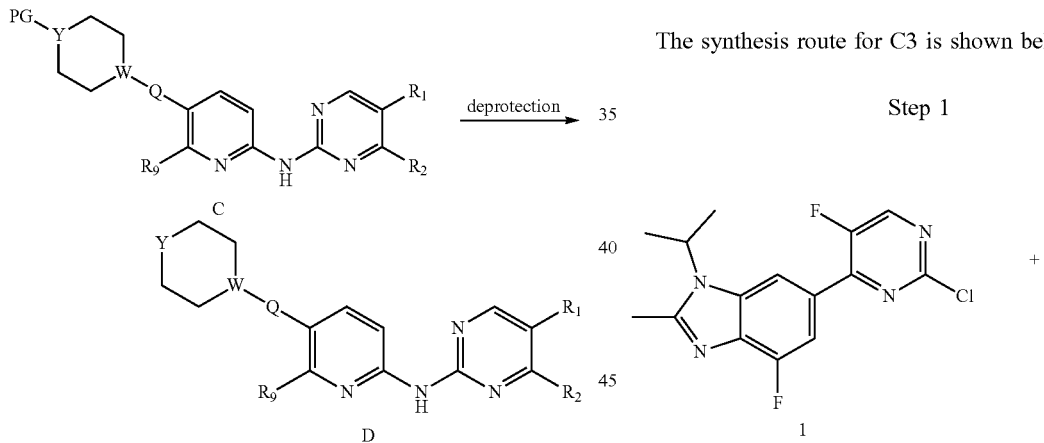

Appropriate deprotection conditions can be used remove PG from Y. For example, when Y-PG is N-tert-butoxycarbonyl (Boc), the Boc group is removed in strong acid (e.g., HCl) to produce the free amine (D).

Step 3: Coupling of L-M to Y

44

-continued

L-M may be coupled to (D) by any suitable conditions depending on the functional groups that are used to form the bond, including palladium catalyzed coupling (e.g., to a primary amine) or amide bond formation. For example, when L has a carboxylic acid (or derivative thereof) and Y is N, EDC (1-Ethyl-3-(3-dimethylaminopropyl)carbodiimide) may be used to form an amide bond (e.g., M) to L.

Those skilled in the art will recognize that the above reactions may be carried out under different conditions, with different catalysts, different protecting groups, and the like, e.g., depending on the compounds to be coupled and the reactions to be carried out.

Synthetic Example 2. Synthesis of C3

The synthesis route for C3 is shown below:

Step 1

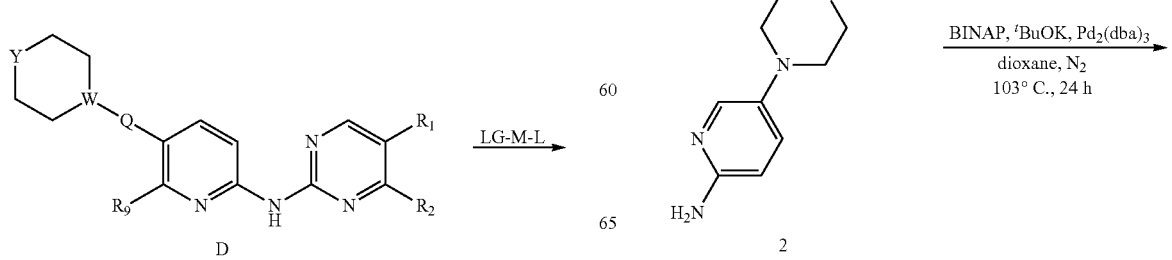

-continued
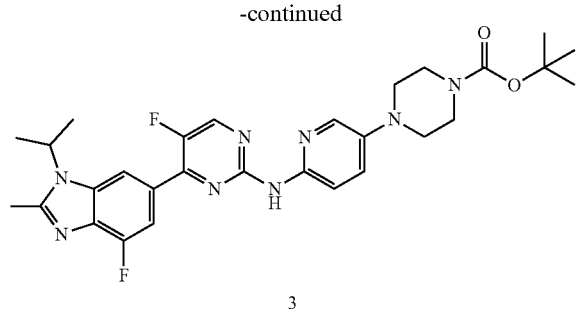
3
Step 2
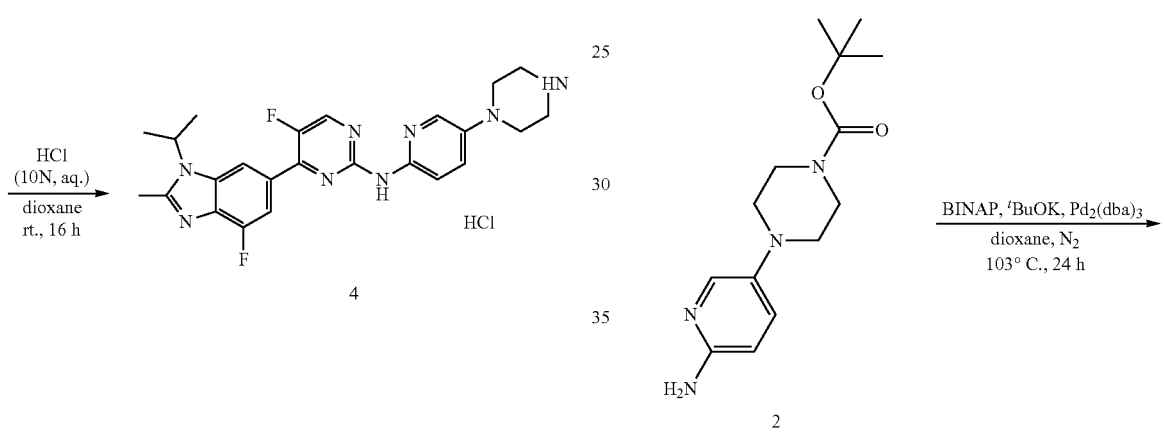
Step 1: Synthesis of Compound 3
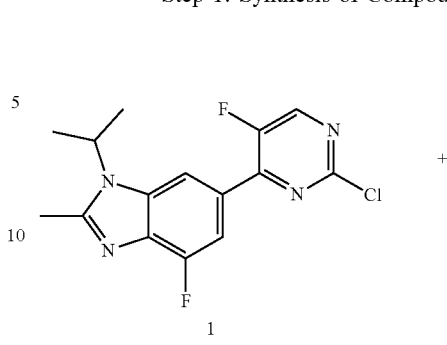
Step 3
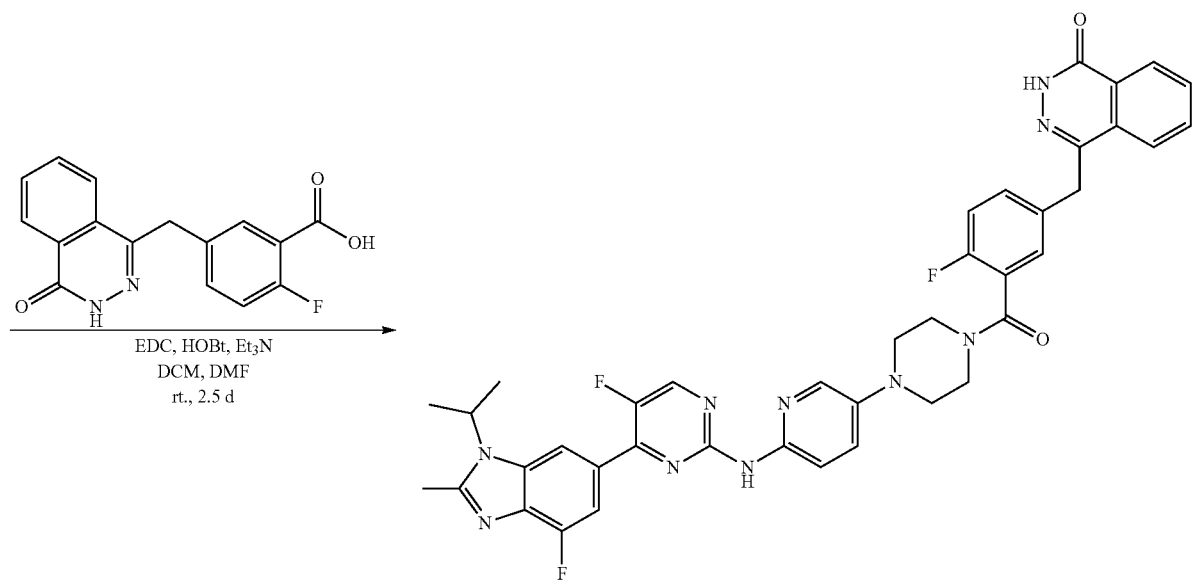

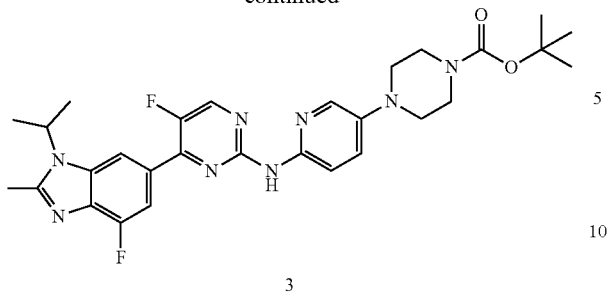

3

To the solution of compound 1 (20.0 g, 62.0 mmol, 1 eq) and 2 (17.3 g, 62.0 mmol, 1 eq) in dioxane (500 mL) were added BINAP (4.8 g, 7.8 mmol, 0.125 eq), $^t$BuOK (8.7 g, 77.5 mmol, 1.25 eq) and Pd$_2$(dba)$_3$ (3.4 g, 3.7 mmol, 0.06 eq). The reaction mixture was stirred under N$_2$ at 103° C. for 24 h, followed by hot filtration. The filtrate was concentrated in vacuo and the residue was poured into water. The resulting mixture was filtrated. The filter cake was rinsed with water (150 mL×2) and EtOAc (150 mL×2) successively, and then dried to afford the product 3 (22.5 g, 64%). $^1$H NMR (400 MHz, DMSO) δ 9.81 (s, 1H), 8.64 (d, J=3.9 Hz, 1H), 8.26 (s, 1H), 8.06 (dd, J=12.5, 6.0 Hz, 2H), 7.67 (d, J=12.3 Hz, 1H), 7.44 (dd, J=9.1, 3.0 Hz, 1H), 4.85 (m, 1H), 3.49-3.47 (m, 4H), 3.09-3.07 (m, 4H), 2.64 (s, 3H), 1.62 (d, J=6.9 Hz, 6H), 1.43 (s, 9H).

Step 2: Synthesis of Compound 4

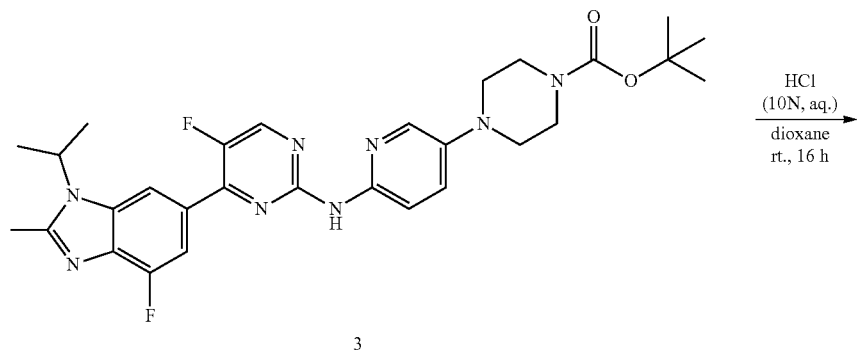

3

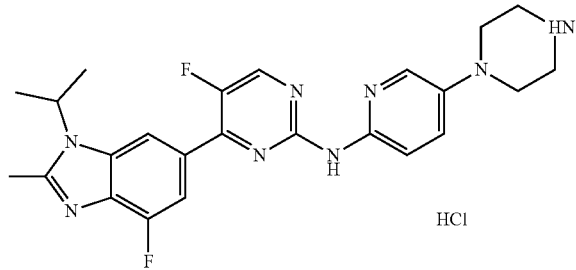

4

To the solution of compound 3 (15.0 g, 26.6 mmol) in dioxane (200 mL) was added HCl (aq., 10 N, 400 mL) slowly and the mixture was stirred at room temperature for about 16 h. After the product was precipitated, the mixture was concentrated in vacuo. The product was rinsed with ether (150 mL×2) and dried in vacuo to afford the product 4 (9.5 g, 70%). $^1$H NMR (400 MHz, DMSO) δ 12.01 (s, 1H), 9.73 (s, 2H), 8.92 (s, 1H), 8.40 (s, 1H), 8.24 (d, J=8.7 Hz, 1H), 7.99 (d, J=2.6 Hz, 1H), 7.90 (m, 2H), 5.07-4.96 (m, 1H), 3.54-3.48 (m, 4H), 3.28-3.19 (m, 4H), 2.84 (s, 3H), 1.67 (d, J=6.8 Hz, 6H).

Step 3. Synthesis for Compound 6

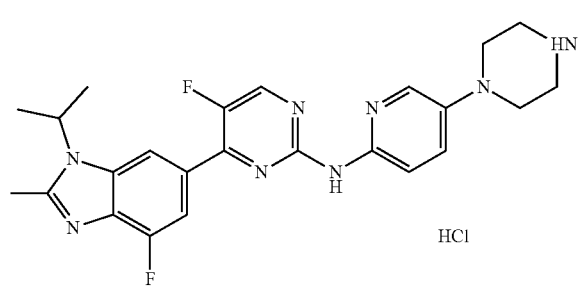

4 HCl

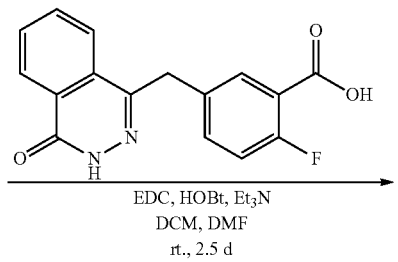

EDC, HOBt, Et$_3$N
DCM, DMF
rt., 2.5 d

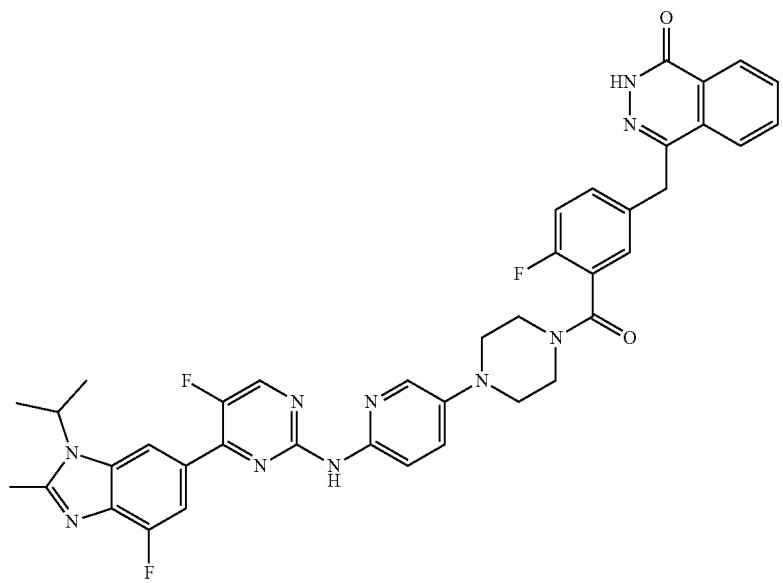

6

To the solution of compound 4 (7 g, 14.0 mmol, 1.0 eq) in the DCM (175 mL) and DMF (10 mL) were added EDCI (3.0 g, 15.4 mmol, 1.1 eq), TEA (20 mL), HOBT (2.3 g, 16.8 mmol, 1.2 eq) and compound 5 (4.6 g, 15.4 mmol, 1.1 eq) at 0° C. The reaction mixture was stirred at room temperature for 2.5 d. The precipitate was filtered, rinsed with DCM (200 mL), EtOAc (150 mL×3) and H$_2$O (200 mL×2) successively and then dried. The solid obtained was rinsed with EtOAc (300 mL) and dried at 65° C. overnight to afford the product 6 (7.4 g, 71%). $^1$H NMR (400 MHz, DMSO) δ 12.60 (s, 1H), 9.85 (s, 1H), 8.63 (d, J=3.5 Hz, 1H), 8.26 (d, J=7.7 Hz, 2H), 8.14-8.02 (m, 2H), 7.98 (d, J=8.0 Hz, 1H), 7.90 (t, J=7.4 Hz, 1H), 7.83 (t, J=7.4 Hz, 1H), 7.67 (d, J=12.0 Hz, 1H), 7.50-7.36 (m, 3H), 7.25 (t, J=8.9 Hz, 1H), 4.83 (dt, J=13.6, 6.7 Hz, 1H), 4.34 (s, 2H), 3.84-3.72 (m, 2H), 3.33 (m, 2H), 3.23-3.13 (m, 2H), 3.09-2.99 (m, 2H), 2.63 (s, 3H), 1.61 (d, J=6.8 Hz, 6H).

BIOLOGICAL EXAMPLES

Biological Example 1. Docking of C3 in PARP1 and CDK

Figure 4:
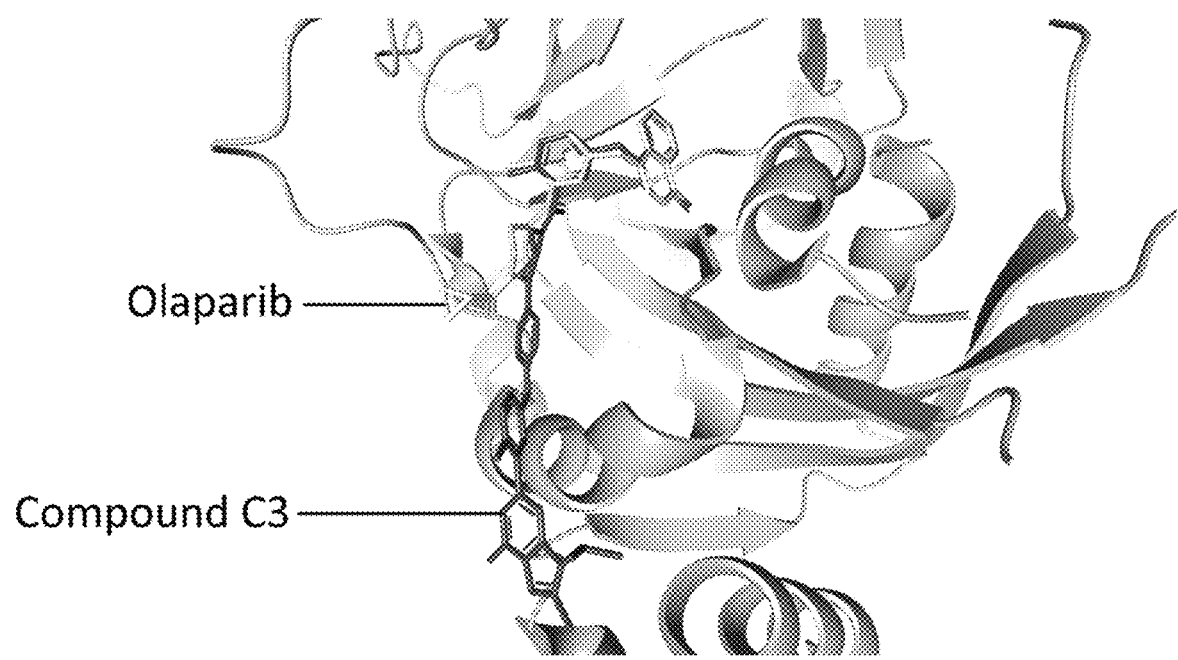
FIG. 4 depicts the binding of C3 and olaparib to PARP1.
Figure 5:
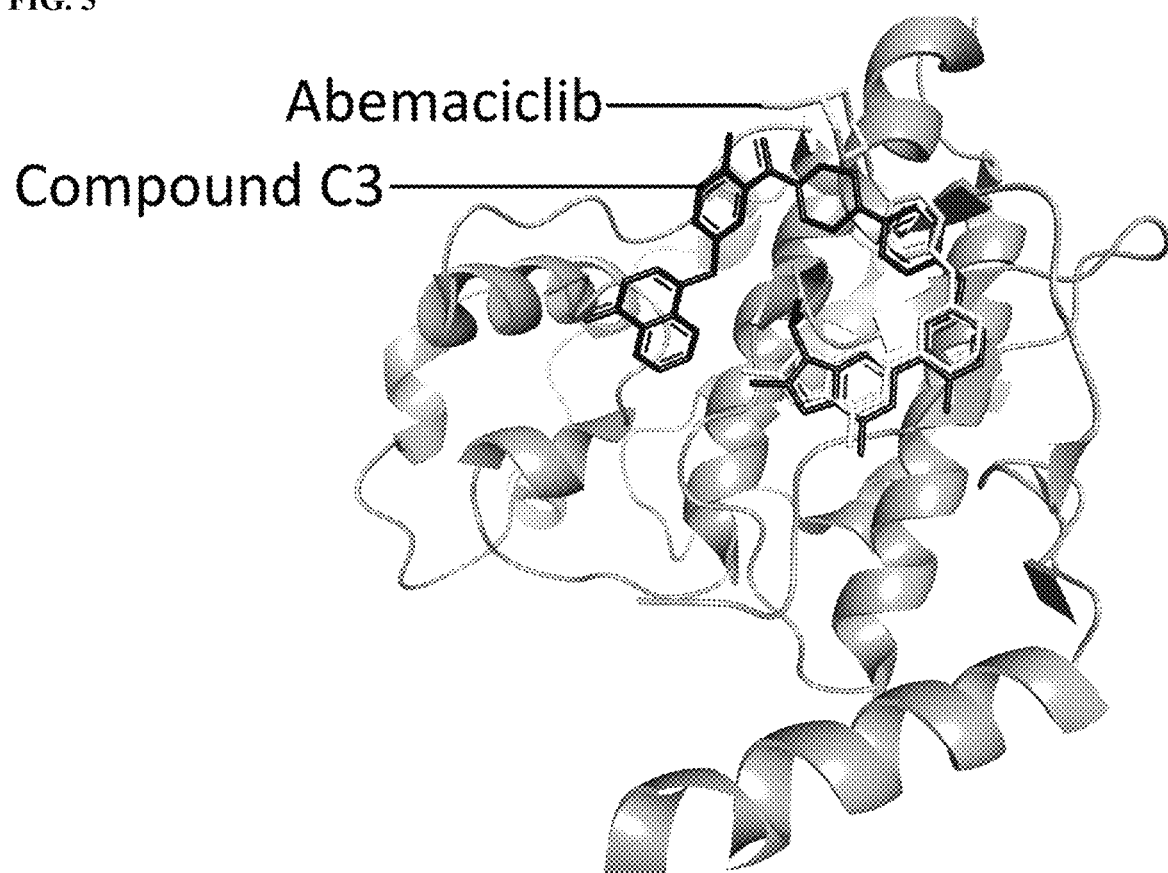
FIG. 5 illustrates the binding of C3 and abemaciclib to CDK.

Computer modeling was used to demonstrate the docking of C3 and olaparib in PARP1 (FIG. 4), and the docking of C3 and abemaciclib in CDK (FIG. 5).

Biological Example 2. Crystal Structure of C3 Complexed to CDK6

Figure 16:
FIG. 16 depicts binding of C3 to CDK6.
Figure 16:
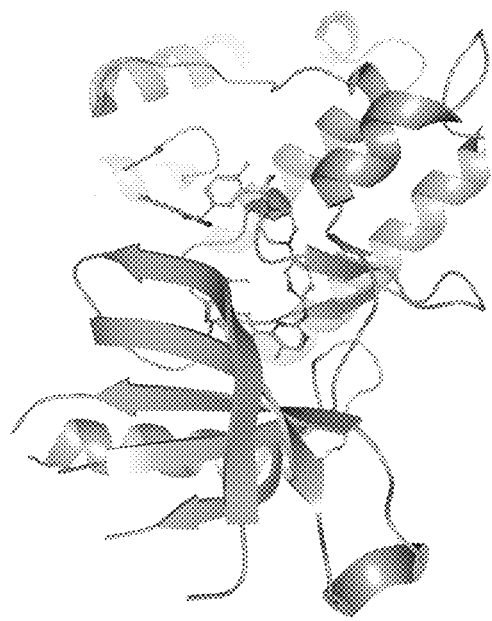

The crystal structure of C3 complexed to CDK6 is provided in FIG. 16. The crystal structure was solved at 2.77 Å.

Biological Example 3. PARP Inhibition Assay

The PARP inhibition assay was performed using a commercially available PARP inhibition assay kit (TREVIGEN, 4690-096-K).

Part 1:

A 1× buffer was prepared by diluting 10× buffer with dH$_2$O.

The nicotinamide adenine dinucleotide (NAD) standards were prepared by diluting the NAD stock solution with the 1× buffer as provided in Table 2 below.

TABLE 2

| 2×NAD standard | Volume of 2 uM NAD stock | Volume of 1× buffer |
|---|---|---|
| 2 uM | 3.5 ml provided | x |
| 1000 nM | 125 ul | 125 ul |
| 500 nM | 65 ul | 195 ul |
| 200 nM | 25 ul | 225 ul |
| 100 nM | 13 ul | 247 ul |
| 20 nM | 3 ul | 297 ul |
| 0 nM | x | 250 ul |

PARP1 inhibitors were prepared in 1× buffer at 50× final concentration. 1 μl of PARP inhibitors were added to the 96 well plate.

PARPminus (×20) and PARPplus (×40) solutions were prepared as provided below in Table 3.

TABLE 3

|  | Minus | plus |
|---|---|---|
| 10× buffer | 5 ul | 5 ul |
| Activated DNA | 5 ul | 5 ul |
| dH2O | 15 ul | 14 ul |
| PARPI Enzyme |  | 1 ul |
| Total volume of PARP mix | 25 ul | 25 ul |

The cycling mix(60×) was prepared as provided below in Table 4.

TABLE 4

|  | 1 well |
|---|---|
| dH2O | 33.9 μl |
| 10× buffer | 5.0 μl |
| Reagent EtOH (95%) | 1.1 μl |
| 10× Resazurin | 5.0 μl |
| 10× cycling enzymes | 5.0 μl |
| Total volume | 50.0 μl |

Part 2:

In the black 96 well plate provided with the kit, 25 μl of 1× buffer was added to wells A5 and A6. To wells B5 to G6, 25 μl of 2×NAD standards were added. To wells H1, H2, A7 to G12, 25 μl NAD2 μM were added. To wells A5 to H6, 1 μl DMSO were added.

The following stock solutions of olaparib and C3 were separately prepared: 500 nM, 2.5 μM, 5 μM, 25 μM, 50 μM, 0.5 mM, and 1 mM. The final concentrations of C3 tested were 10 nM, 20 nM, 50 nM, 100 nM, 500 nM, 1 μM, 10 μM, and 20 μM. Similarly, the final olaparib concentrations tested were as follows: 10 nM, 20 nM, 50 nM, 100 nM, 500 nM, 1 μM, 10 μM, and 20 μM.

The following stock solutions of abemaciclib (C2) were prepared: 0.5 mM, 1 mM, 5 mM, and 10 mM. The final concentrations of C2 tested were 20 μM, 100 μM, and 200 μM.

To wells A7 to G12, 1 μl 50× inhibitors were added.

The 96 well plate is shown in Table 5.

TABLE 5

|  | 5 | 6 | 7 olaparib | 8 olaparib | 9c3 | 10c3 | 11c2 | 12c2 |
|---|---|---|---|---|---|---|---|---|
| A | blank | blank | 10 nM | 10 nM | 10 nM | 10 nM | 10 uM | 10 μM |
| B | NAD 10 nM | NAD 10 nM | 20 nM | 20 nM | 20 nM | 20 nM | 20 μM | 20 μM |
| C | 50 nM | 50 nM | 50 nM | 50 nM | 50 nM | 50 nM | 100 μM | 100 μM |
| D | 100 nM | 100 nM | 100 nM | 100 nM | 100 nM | 100 nM | 200 uM | 200 uM |
| E | 250 nM | 250 nM | 500 nM | 500 nM | 500 nM | 500 nM | Olaparib inhibitor control | Olaparib inhibitor control |
| F | 500 nM | 500 nM | 1 μM | 1 μM | 1 μM | 1 μM | C2 inhibitor control | C2 inhibitor control |
| G | 1 μM NAD | 1 μM NAD | 10 μM | 10 μM | 10 μM | 10 μM | C3 inhibitor control | C3 inhibitor control |
| H | 1 μM NAD/ PARP | 1 μM NAD/ PARP | 20 μM | 20 μM |  |  |  |  |

25 μl of PAPRminus was added to yellow colored wells, and mixed.

25 μl of PAPRplus was added to pink colored wells, and mixed.

The reaction was allowed to proceed for 30 min at room temperature (RT).

50 μl of cycling mix was added to all wells, and mixed.

The reaction was allowed to proceed for 30 min at RT.

50 μl of stop solution was added to all wells, and mixed.

The 96 well plate was read with a fluorescent plate reader (544 nm excitation/590 nm emission filters).

The final PARP concentration was 40 nM.

Figure 1B:
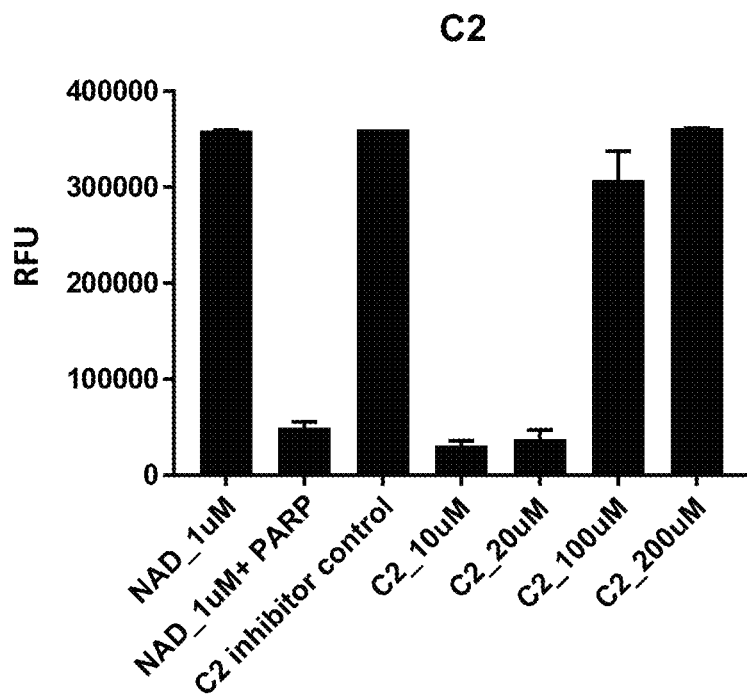
FIG. 1B graphically illustrates the activity of PARP1 in the presence of increasing concentrations of C2 (Abemaciclib) in terms of RFU.
Figure 1C:
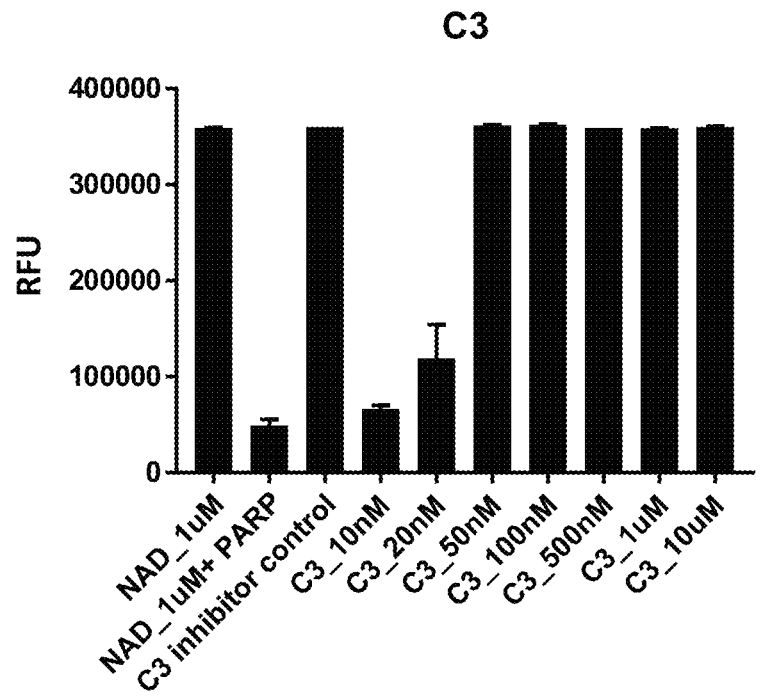
FIG. 1C graphically illustrates the activity of PARP1 in the presence of increasing concentrations of C3 in terms of RFU.
Figure 1D:
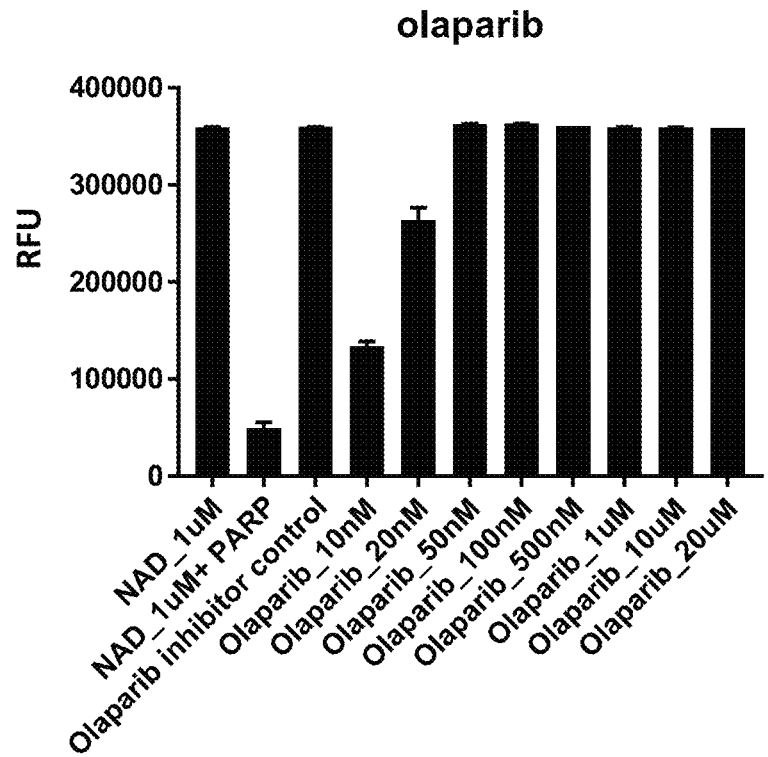
FIG. 1D graphically illustrates the activity of PARP1 in the presence of increasing concentrations of olaparib in terms of RFU.

The fluorescence (RFU) of the wells containing NAD, in the absence of PARP1 or an inhibitor, are reported in FIG. 1A. The standards indicate that higher concentrations of NAD correspond to higher fluorescence. Because PARP1 consumes NAD, PARP1 inhibition was determined by fluorescence intensity. FIG. 1B shows PARP1 inhibition measured for C2 (Abemaciclib). FIG. 1C shows PARP1 inhibition measured for C3, and FIG. 1D shows PARP1 inhibition measured for olaparib.

Figure 2A:
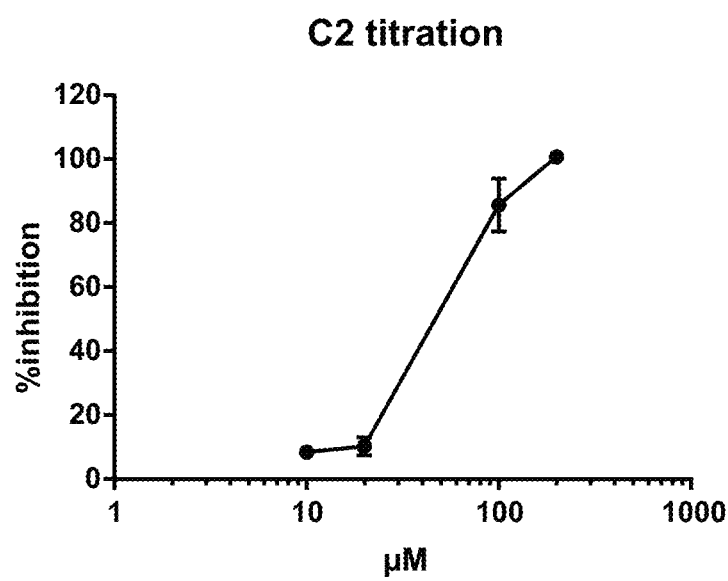
FIG. 2A graphically illustrates the PARP1 inhibition curve for the C2 (Abemaciclib).
Figure 2B:
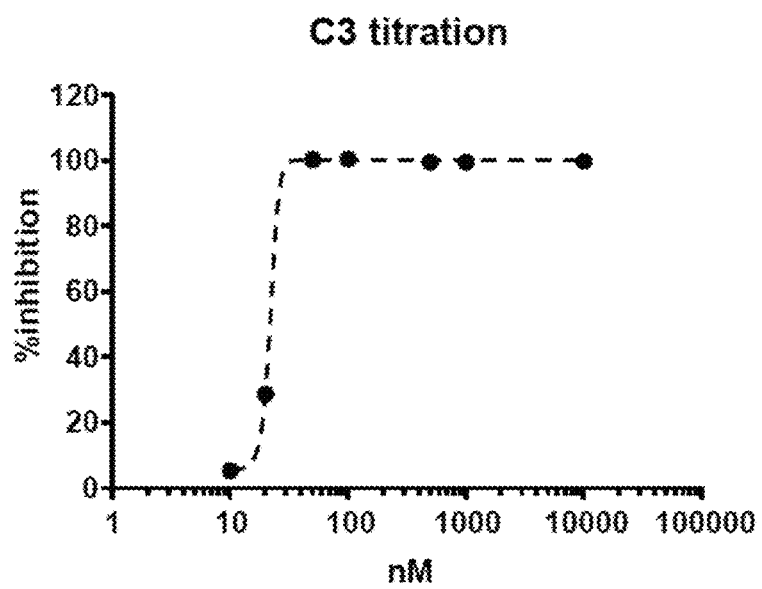
FIG. 2B graphically illustrates the PARP1 inhibition curve for C3.
Figure 2C:
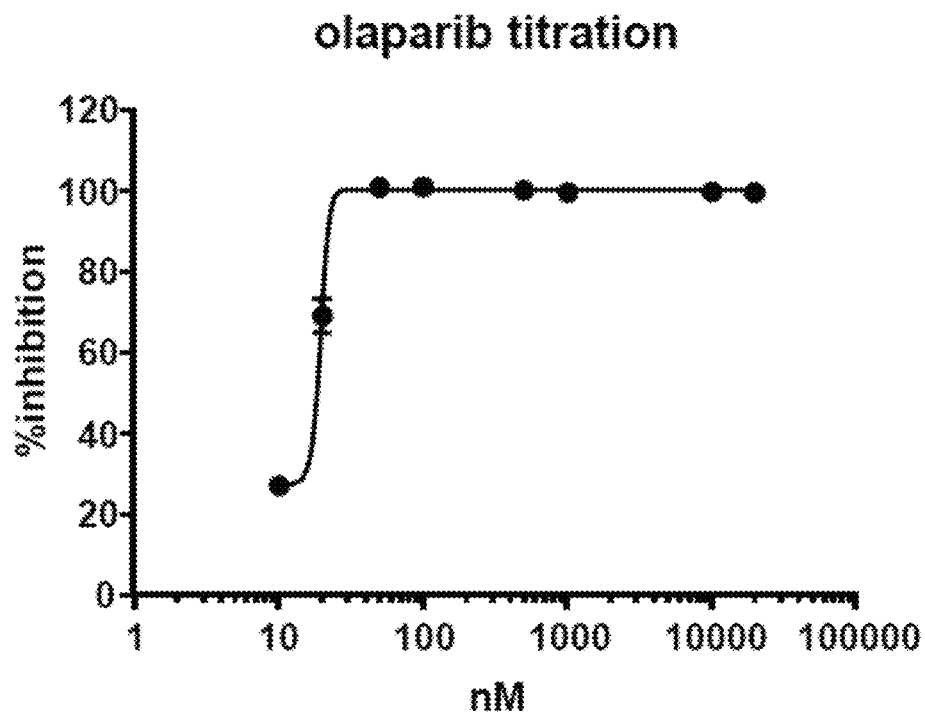
FIG. 2C graphically illustrates the PARP1 inhibition curve for olaparib.
Figure 2D:
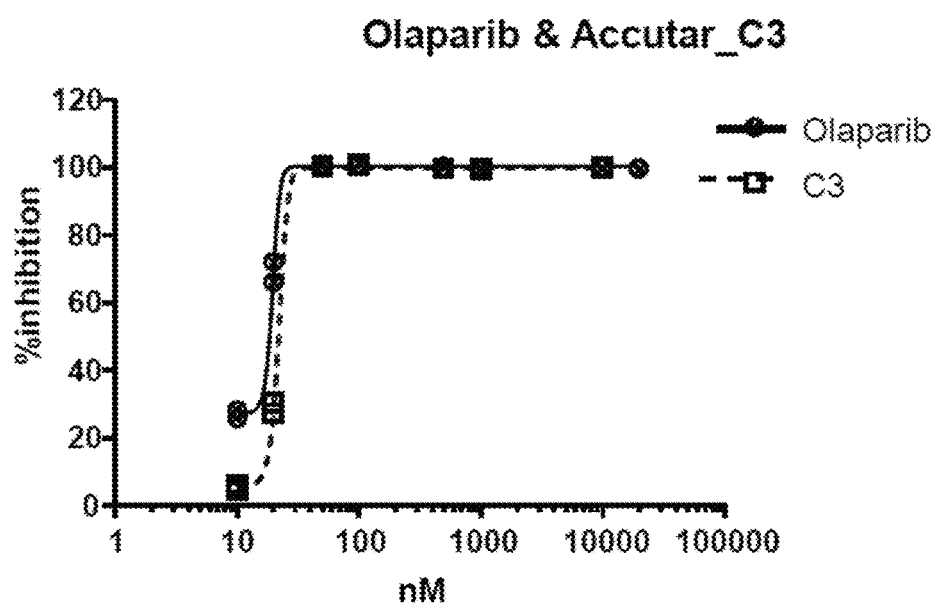
FIG. 2D is a graphical comparison of the PARP1 inhibition curve for olaparib and C3.

Inhibition curves were prepared based on the fluorescence data. FIG. 2A shows the PARP1 inhibition curve for the C2 (Abemaciclib). FIG. 2B shows the PARP1 inhibition curve for C3. FIG. 2C shows the PARP1 inhibition curve for olaparib. FIG. 2D compares the PARP1 inhibition curve for C3 and the strongest FDA-approved PARP1 inhibitor, olaparib.

These results indicate that C3 is superior to C2 (Abemaciclib) and similar to olaparib as a PARP1 inhibitor.

Biological Example 4. CDK Inhibition Assay

In 96 semi area plate (VWR 33501-814), we added substrates, enzyme, and inhibitors for a total volume of 15 µl per well. The mixture contains 0.1 ug/ul histoneH1, 250 uM ATP, CDK/cyclinD3 60 ng (Promega V4511), and tested inhibitor C2 (Abemaciclib) or C3 with final concentration of 0 nM, 5 nM, 10 nM, 20 nM, 39 nM, 78 nM, 156 nM, 313 nM, 625 nM, 1.25 µm, 2.50 µM, 5 µM, 10 µM. The mixtures were incubated for 60 min at RT. Kinase reactions were stopped by adding 15 µl ADP-Glo (Promega V9101) for 40 min RT, followed by adding 30 µl Kinase Detection Reagent (Promega V9101) for 30 min RT. Luminescence signal from the plate was recorded with EnSpire Multimode Plate Reader (PerkinElmer) (integration time 0.5 second).

Figure 3A:
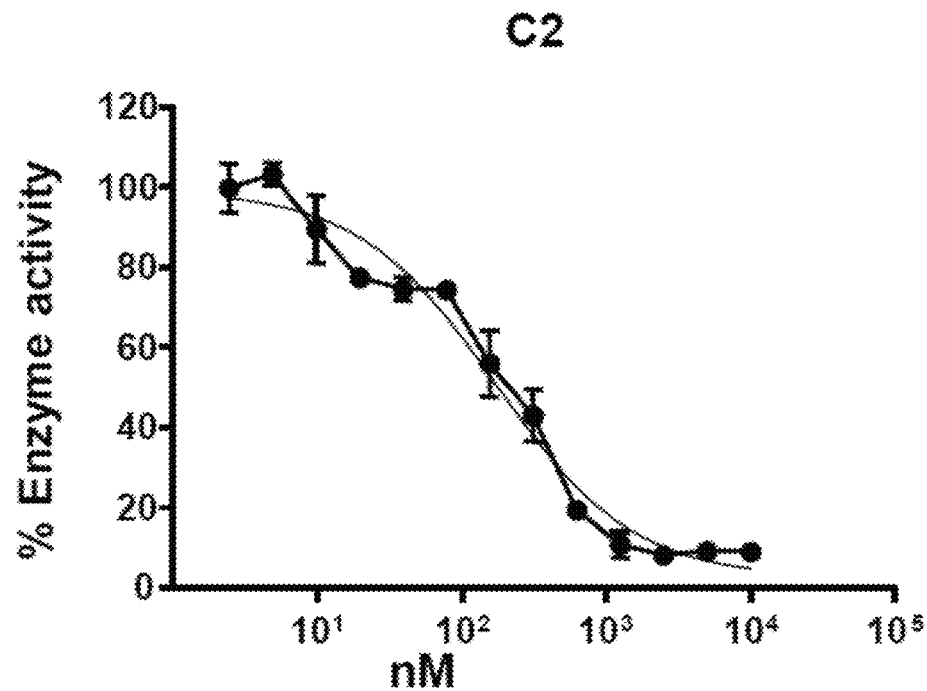
FIG. 3A graphically illustrates the enzyme activity of CDK6 over increasing concentrations of C2 (Abemaciclib).
Figure 3B:
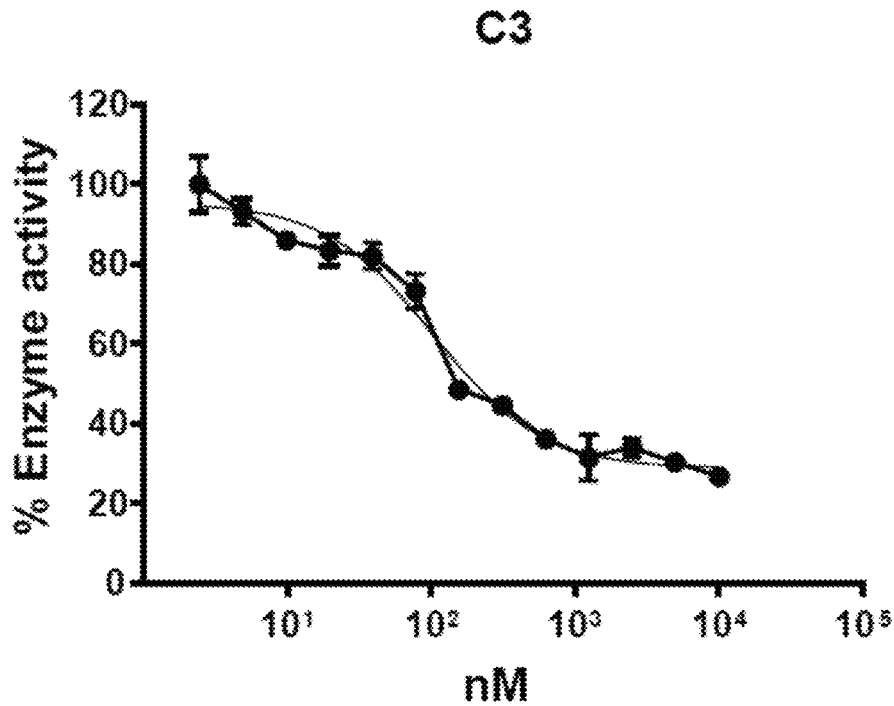
FIG. 3B graphically illustrates the enzyme activity of CDK6 over increasing concentrations of C3.
Figure 3C:
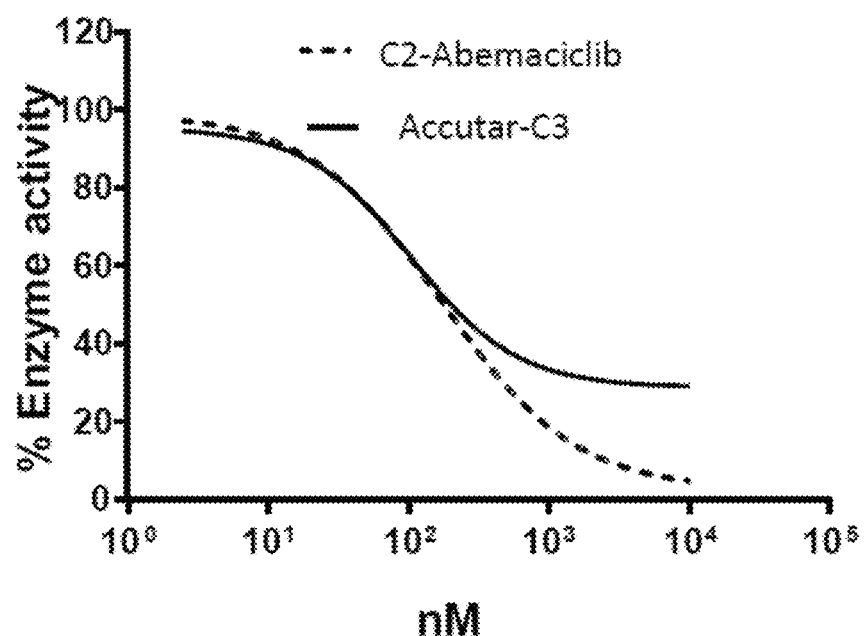
FIG. 3C is a graphical comparison of the CDK6 inhibition curves for C2 (Abemaciclib) and C3.

CDK inhibition curves were prepared for C2 (Abemaciclib) (FIG. 3A) and C3. FIG. 3C shows a comparison of the CDK6 inhibition curves for C2 (Abemaciclib) and C3.

These results indicate that C3 has a similar CDK6 inhibitory activity as C2 (Abemaciclib).

Biological Example 5. MCF7 Cell Proliferation Assay

Figure 6A:
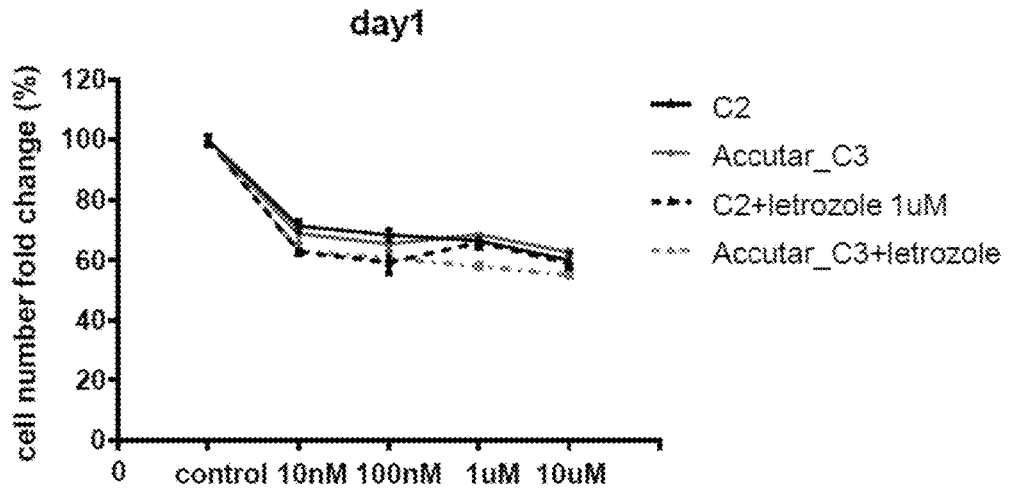
FIG. 6A graphically illustrates the MCF7 cell proliferation results at increasing concentrations of C2 (Abemaciclib), C2 and letrozole (1 µM), C3, and C3 in combination with letrozole (1 µM) measured at day 1.
Figure 6B:
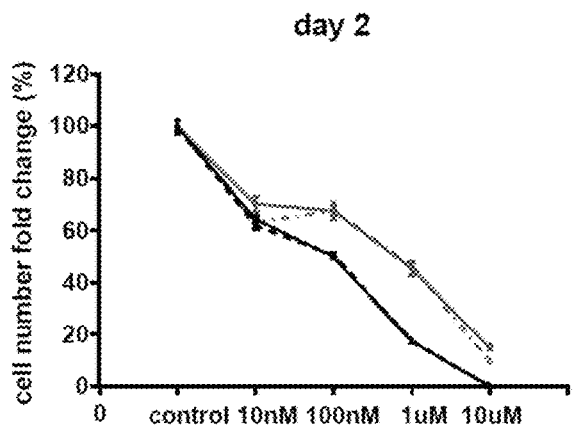
FIG. 6B graphically illustrates the MCF7 cell proliferation results at increasing concentrations of C2, C2 and letrozole (1 µM), C3, and C3 in combination with letrozole (1 µM) measured at day 2.
Figure 6C:
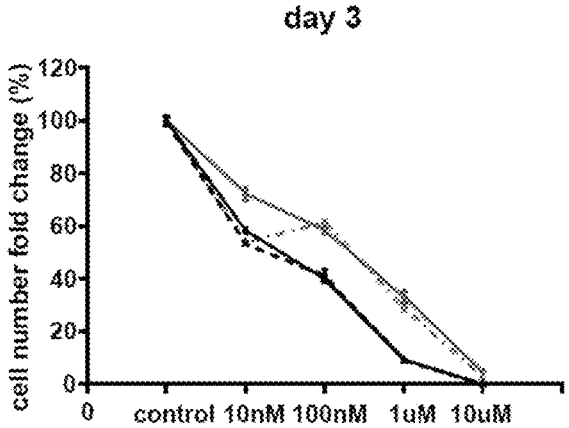
FIG. 6C graphically illustrates the MCF7 cell proliferation results at increasing concentrations of C2, C2 in combination with letrozole (1 µM), C3, and C3 in combination with letrozole (1 µM) measured at day 3.
Figure 6D:
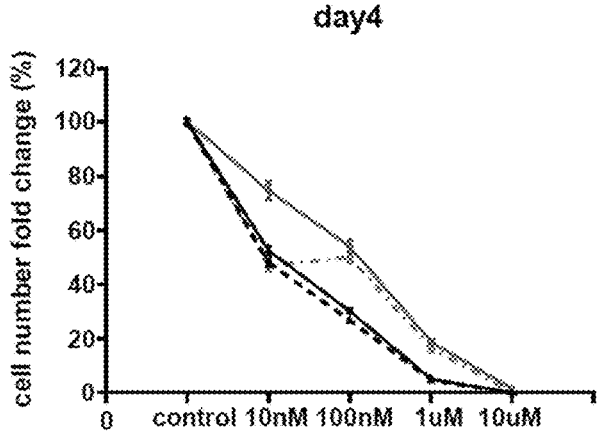
FIG. 6D graphically illustrates the MCF7 cell proliferation results at increasing concentrations of C2, C2 in combination with letrozole (1 µM), C3, and C3 in combination with letrozole (1 µM) measured at day 4.
Figure 7A:
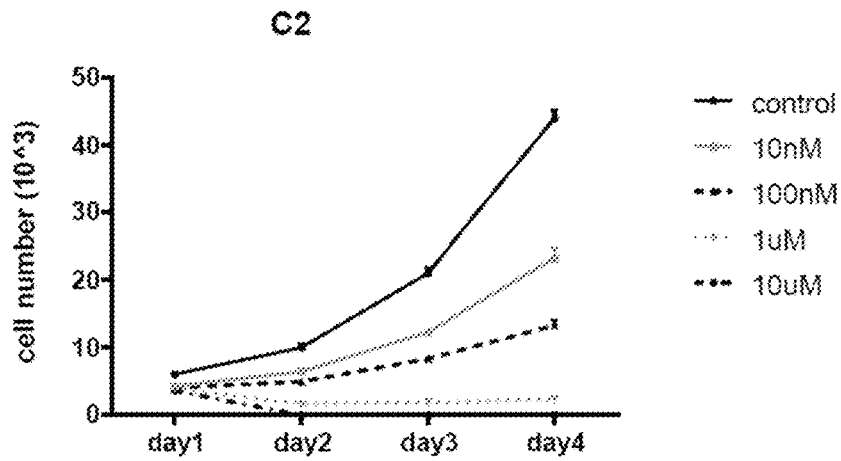
FIG. 7A graphically illustrates the MCF7 cell proliferation results at increasing concentrations of C2 measured for days 1-4.
Figure 7B:
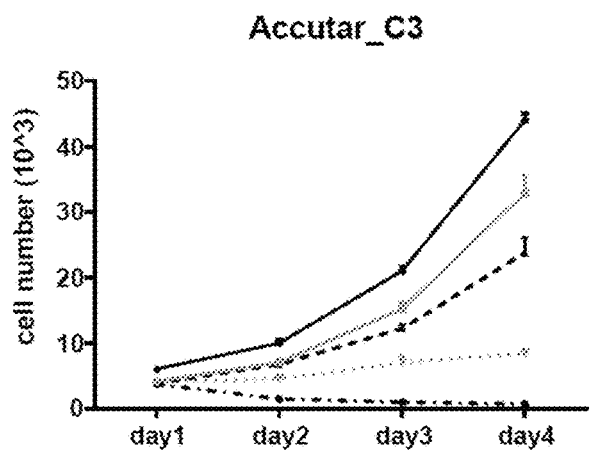
FIG. 7B graphically illustrates the MCF7 cell proliferation results at increasing concentrations of C3 measured at days 1-4.
Figure 7C:
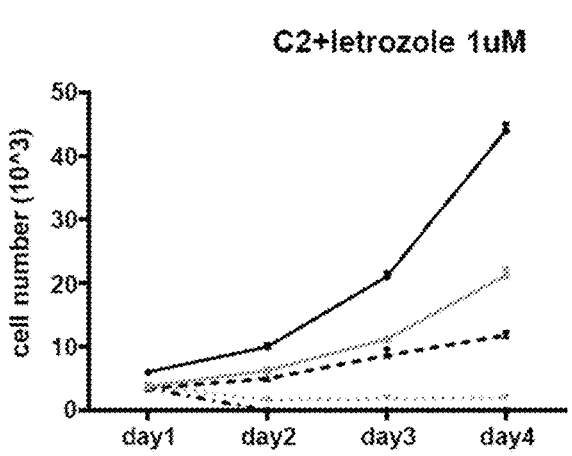
FIG. 7C graphically illustrates the MCF7 cell proliferation results at increasing concentrations of C2 in combination with letrozole (1 µM) measured at days 1-4.
Figure 7D:
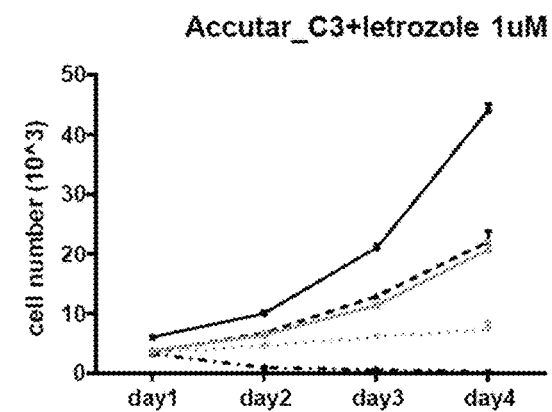
FIG. 7D graphically illustrates the MCF7 cell proliferation results at increasing concentrations of C3 in combination with letrozole (1 µM) measured at days 1-4.

A cell proliferation assay was performed with MCF7 cells, which is a human breast cancer adenocarcima cell line which expresses PARP1, to compare the inhibitor effect of C2 (Abemaciclib), C2 in combination with letrozole (1 µM), C3, and C3 in combination with letrozole (1 µM). Cell proliferation results at increasing concentrations of C2 and C3 were measured at day 1 (FIG. 6A), day 2 (FIG. 6B), day 3 (FIG. 6C), and day 4 (FIG. 6D). The cell proliferation results for each treatment over days 1-4 are provided in FIG. 7A-7D.

These results indicate that C3 is an inhibitor of cell proliferation of MCF7 human breast cancer adenocarcima cells.

Biological Example 6. MB231 Cell Proliferation Assay

Figure 8A:
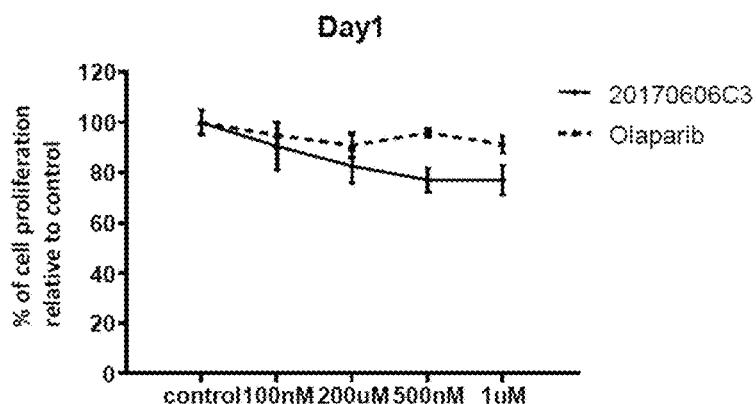
FIG. 8A graphically illustrates the MB231 cell proliferation results at increasing concentrations of C3 and olaparib measured at day 1.
Figure 8B:
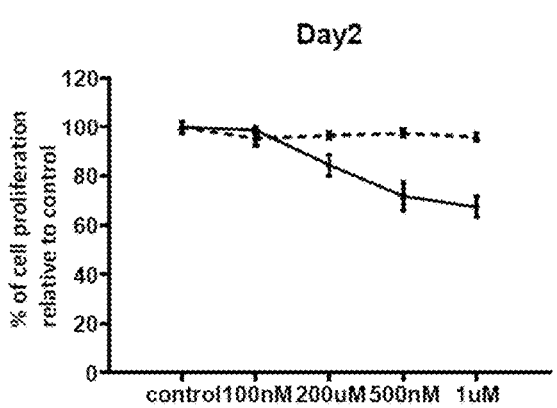
FIG. 8B graphically illustrates the MB231 cell proliferation results at increasing concentrations of C3 and olaparib measured at day 2.
Figure 8C:
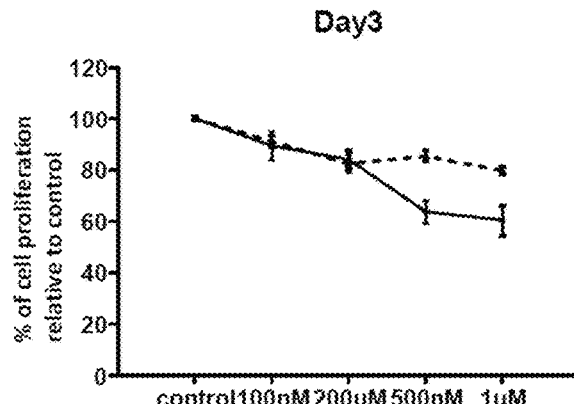
FIG. 8C graphically illustrates the MB231 cell proliferation results at increasing concentrations of C3 and olaparib measured at day 3.
Figure 8D:
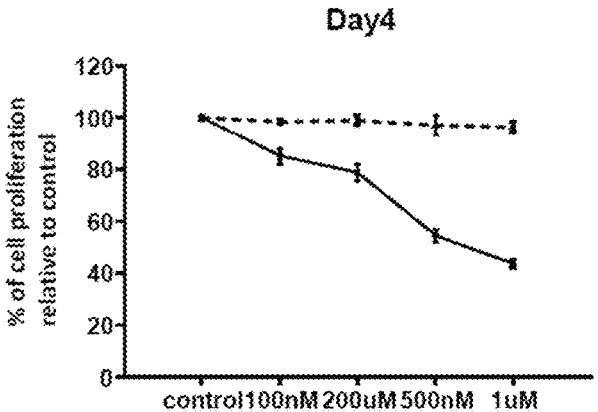
FIG. 8D graphically illustrates the MB231 cell proliferation results at increasing concentrations of C3 and olaparib measured at day 4.
Figure 9A:
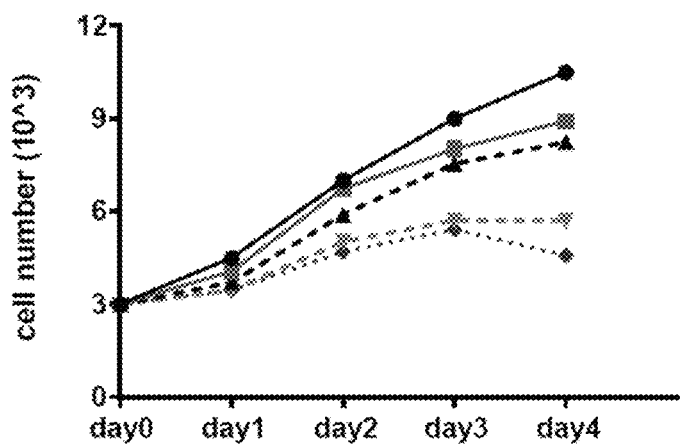
FIG. 9A graphically illustrates the MB231 cell proliferation results at increasing concentrations of C3 measured for days 1-4.
Figure 9B:
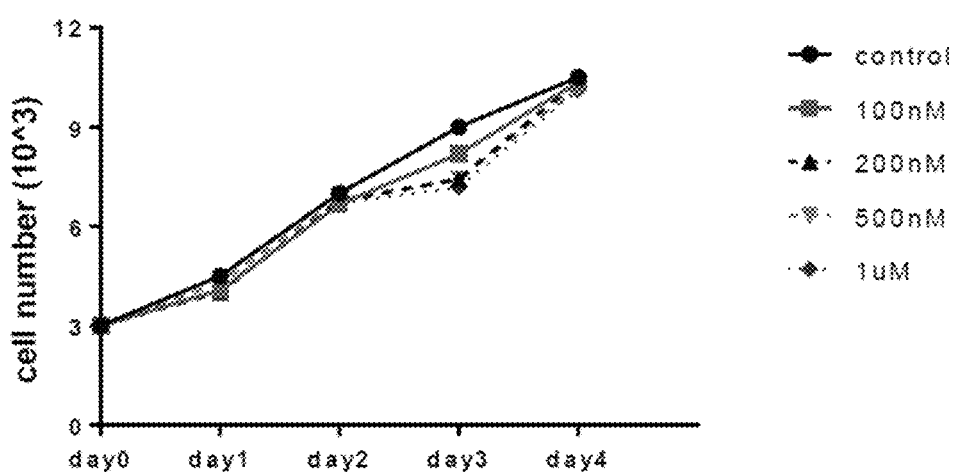
FIG. 9B graphically illustrates the MB231 cell proliferation results at increasing concentrations of olaparib measured at days 1-4.

A cell proliferation assay was performed with MB231 cells, which is a human breast cancer adenocarcinoma cell line expressing a mutant CDKN2A, treated with C3 or olaparib. Cell proliferation results at increasing concentrations of C3 and olaparib were measured at day 1 (FIG. 8A), day 2 (FIG. 8B), day 3 (FIG. 8C), and day 4 (FIG. 8D). The cell proliferation results for each treatment over days 1-4 are provided in FIGS. 9A and 9B.

These results indicate that C3 is a stronger inhibitor of cell proliferation of MB231 human breast cancer adenocarcinoma cells than olaparib.

Biological Example 7. BRAC1 Mutant Triple Negative Breast Cancer Cell Growth Inhibition Assay HCC1937 cells and HCC1395 cells are both Brad mutant, triple negative (ER, PR, HER2) breast cancer cell lines. The cells were maintained in RPMI1640 medium (Gibco A10491-01) supplemented with 10% FBS, and 1× Penicillin Streptomycin. The HCC1937 cells (ATCC® CRL-2336™) and HCC1395 cells (ATCC® CRL-2324™), respectively, were plated in 96 dark well plates at $0.4 \times 10^4$ cells/well.

Olaparib and C3 were added to medium to achieve a final concentration of 10 nM, 100 nM, 1 µM, and 10 µM, and each had a final volume of 100 µl. Cell medium was replaced each day for 4 days.

To determine cell viability, the relative cell number was determined by the Cell Titer Glo reagent (Promega) according to the protocol. At each day of the assay, the 96 well plate and reagents were equilibrated at RT for 30 min. 100 µl of Cell Titer Glo reagent was added to each well. The contents of each well were mixed using a pipetter to induce cell lysis. The plate was allowed to incubate at RT for 30 min to stabilize the luminescent signal, and the luminescence was determined by a luminometer (Perkin Elmer EnSpire).

Figure 10A:
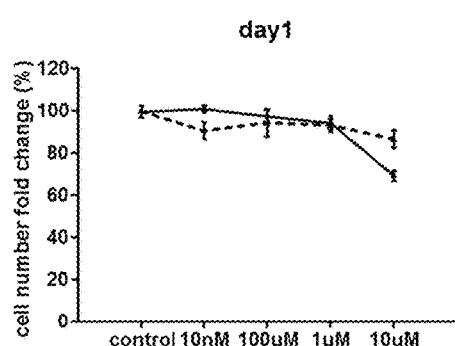
FIG. 10A-D graphically illustrates inhibition of growth (reported as cell number fold change) of HCC1395 cells after 1 day (FIG. 10A), 2 days (FIG. 10B), 3 days (FIG. 10C) and 4 days (FIG. 10D) in the presence of 10 nM, 100 nM, 1 µM, and 10 µM of C3 and olaparib, respectively.
Figure 10B:
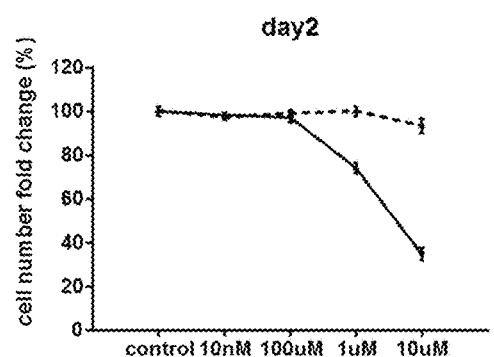
Figure 10C:
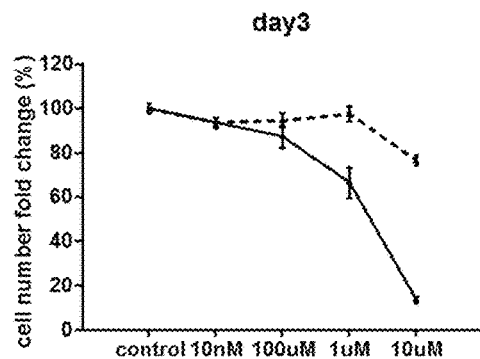
Figure 10D:
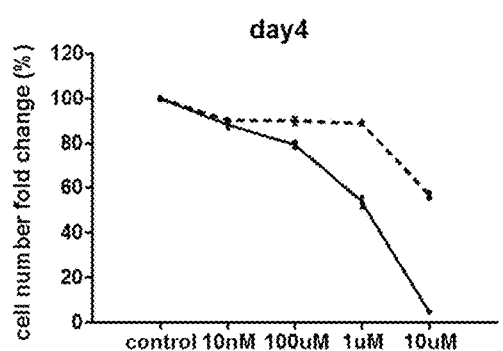
Figure 10E:
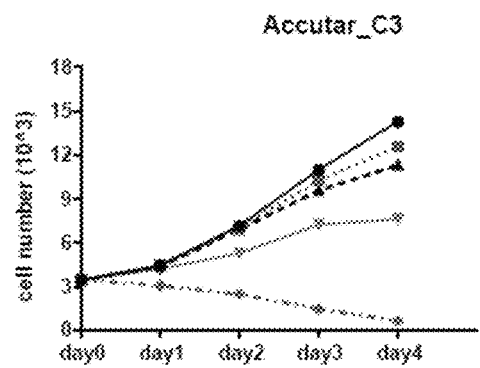
FIG. 10E graphically illustrates the number of HCC1395 cells ($10^3$) measured at day 1, 2, 3, and 4, in the presence of 10 nM, 100 nM, 1 µM, and 10 µM of C3.
Figure 10F:
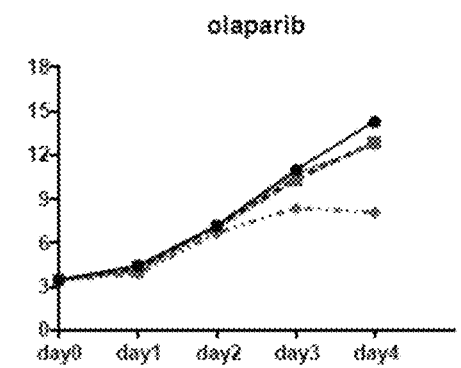
FIG. 10F graphically illustrates the number of HCC1395 cells ($10^3$) measured at day 1, 2, 3, and 4, in the presence of 10 nM, 100 nM, 1 µM, and 10 µM of olaparib.

The results of cancer cell growth inhibition assay with the HCC1395 cell line are shown in FIG. 10A-F. Specifically, FIG. 10D shows that almost no HCC1395 cells were viable after treatment with 10 µM of C3 at day 4, whereas approximately 60% of the HCC1395 cells were viable after treatment with 10 µM of olaparib at 10 µM for 4 days. These results indicate that C3 is a stronger inhibitor of Brac1 mutant, triple negative (ER, PR, HER2) breast cancer cell growth than olaparib.

Figure 11A:
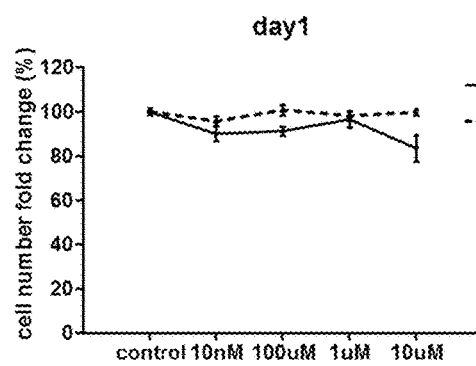
FIG. 11A-D graphically illustrates inhibition of growth (reported as cell number fold change) of HCC1937 cells after 1 day (FIG. 11A), 2 days (FIG. 11B), 3 days (FIG. 11C) and 4 days (FIG. 11D) in the presence of 10 nM, 100 nM, 1 µM, and 10 µM of C3 and olaparib, respectively.
Figure 11B:
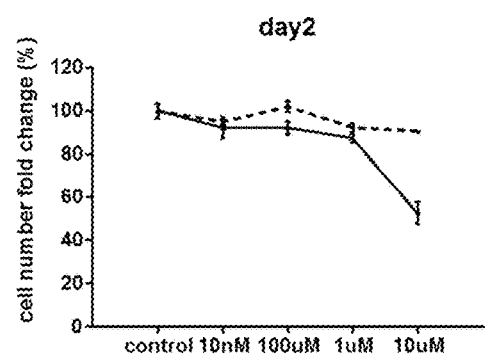
Figure 11C:
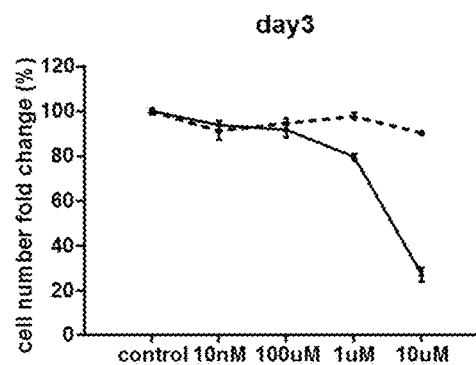
Figure 11D:
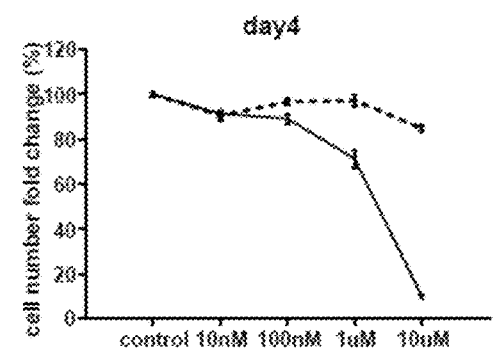
Figure 11E:
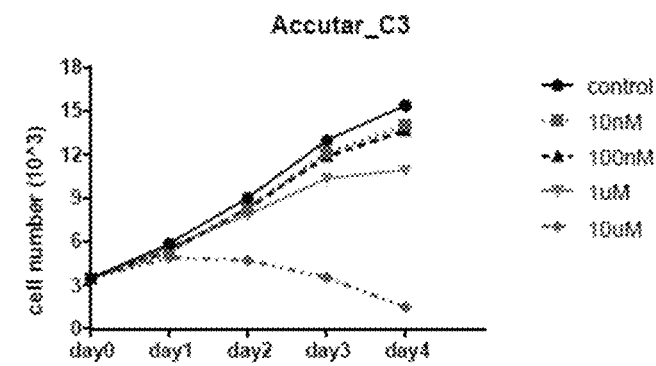
FIG. 11E graphically illustrates the number of HCC1937 cells ($10^3$) measured at day 1, 2, 3, and 4, in the presence of 10 nM, 100 nM, 1 µM, and 10 µM of C3.
Figure 11F:
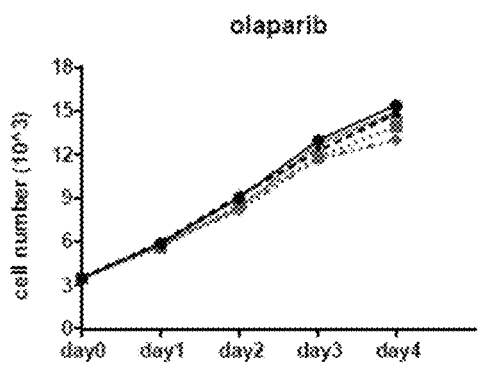
FIG. 11F graphically illustrates the number of HCC1937 cells ($10^3$) measured at day 1, 2, 3, and 4, in the presence of 10 nM, 100 nM, 1 µM, and 10 µM of olaparib.

The results of cancer cell growth inhibition assay with the HCC1937 cell line are shown in FIG. 11A-F. FIG. 11D shows that almost no HCC1937 cells were viable after treatment with 10 µM of C3, whereas more than 80% of the HCC1937 cells were viable after treatment with 10 µM olaparib at day 4. These results indicate that C3 is a stronger inhibitor of Brac1 mutant, triple negative (ER, PR, HER2) breast cancer cell growth than olaparib.

Biological Example 8. Kinase Selectivity

Figure 12:
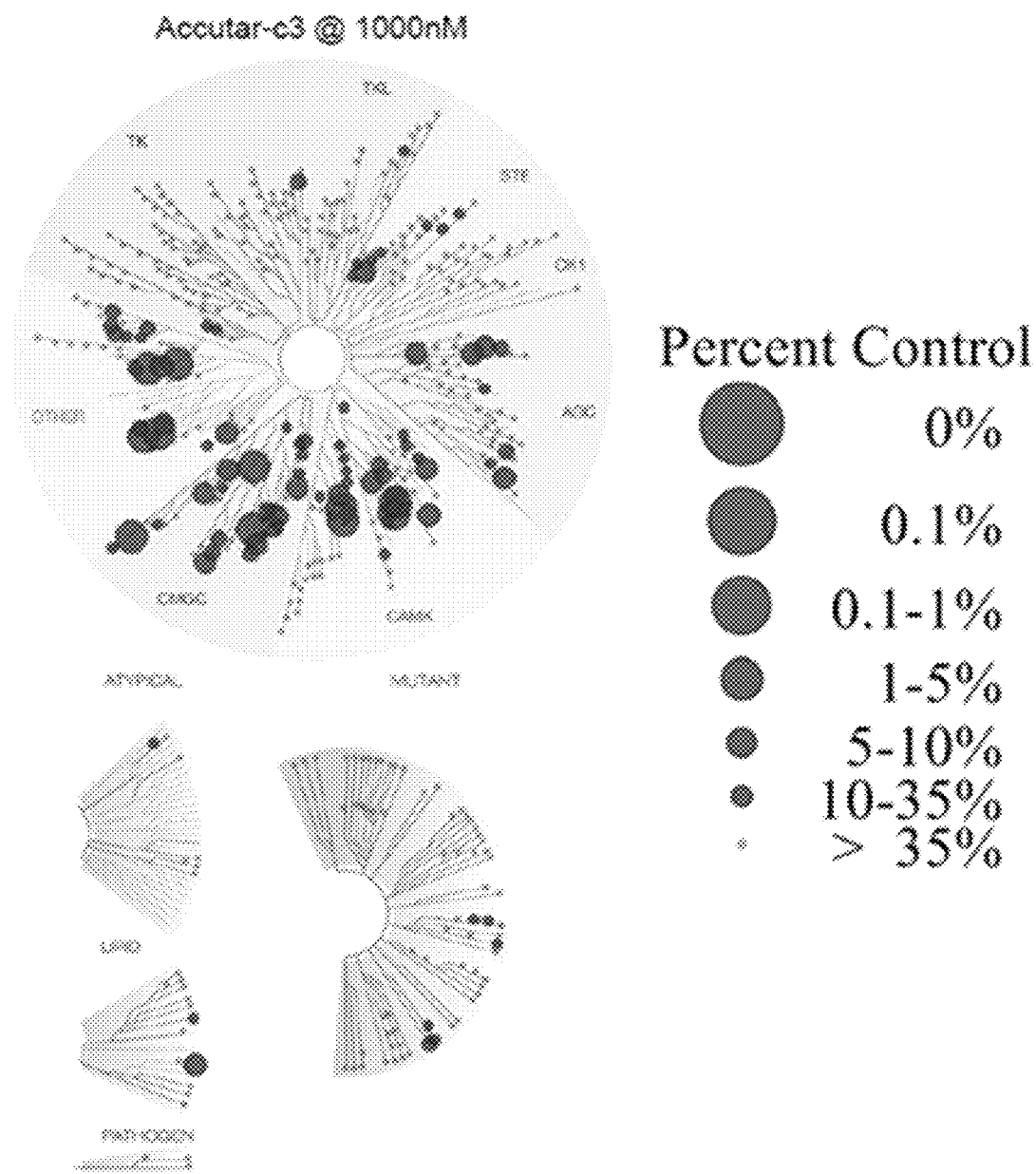
FIG. 12 is a kinase selectivity tree that graphically illustrates the selectivity of C3 for the more than 480 kinases screened.

A kinase selectivity assay was performed with C3 using DiscoverX KINOMEscan™ (www.discoverx.com/, which is herein incorporated by reference in its entirety for all purposes). The KINOMEscan platform employs active site-directed competition binding assay to quantitatively measure interactions between test compounds (e.g., C3) and more than 480 kinase assays including clinically relevant mutants, lipid, atypical, and pathogen kinases, plus a growing panel of activation-state specific assays. The results are provided in Table 6 and FIG. 12.

TABLE 6

| Compound | Selectivity Score Type | Number of Hits | Number of Non-Mutant Kinases | Screening Concentration (nM) | Selectivity Score |
|---|---|---|---|---|---|
| C3 | S(35) | 86 | 403 | 1000 | 0.213 |
| C3 | S(10) | 50 | 403 | 1000 | 0.124 |
| C3 | S(1) | 11 | 403 | 1000 | 0.027 |

The data was interpreted using three selectivity score types (e.g., S(35); S(10); and S(1)) in order to provide a broad kinase selectivity picture (e.g., a selectivity score) of C3. The selectivity score was calculated using % Ctrl as a potency threshold (below) and provides a quantitative method of describing compound selectivity to facilitate comparison of different compounds. The three selectivity score types used to interpret the data are summarized below:

$S$=Number of hits/Number of assays $S(35)$=(number of non-mutant kinases with % Ctrl<35)/(number of non-mutant kinases tested)

$S(10)$=(number of non-mutant kinases with % Ctrl<10)/(number of non-mutant kinases tested)

$S(1)$=(number of non-mutant kinases with % Ctrl<1)/(number of non-mutant kinases tested)

This data indicates that C3 is a relatively selective kinase, with similar kinase selectivity as Abemaciclib.

Biological Example 9. Pharmacokinetics

Pharmacokinetic parameters of the of C3 were measured after a single intraperitoneal injection (IP) of 10 mg/kg, or oral administration (PO) of 50 mg/kg in female BALB/c mice. Pharmacokinetic parameters measured include: elimination half-life ($t_{1/2}$), time to reach maximum blood plasma concentration ($T_{max}$); maximum blood plasma concentration ($C_{max}$); area under the blood plasma concentration-time curve from time zero to the last detectable plasma concentration ($AUC_{(0-t)}$); area under the blood plasma concentration-time curve from time zero to infinity ($AUC_{(0-\infty)}$); the mean residence time of the drug in the body from time zero to the last detectable plasma concentration ($MRT_{(0-t)}$); apparent volume of distribution during terminal phase (Vz); and apparent total body clearance of the drug from plasma (CL). The results are provide in Table 7.

TABLE 7

| Group No. | $t_{1/2}$ (h) | $T_{max}$ (h) | $C_{max}$ (ng/ml) | $AUC_{(0-t)}$ (h*ng/ml) | $AUC_{(0-\infty)}$ (h*ng/ml) | $MRT_{(0-t)}$ (h) | Vz (ml/kg) | CL (ml/h/kg) |
|---|---|---|---|---|---|---|---|---|
| 10 mg/kg Accutar-C3(IP) | 5.7 | 0.25 | 283.74 | 2516.85 | 2673.38 | 6.3 | 30758.32 | 3740.59 |
| 50 mg/kg Accutar-C3(PO) | / | 4 | 291.87 | 1701.9 | / | 3.62 | / | / |

Figure 13A:
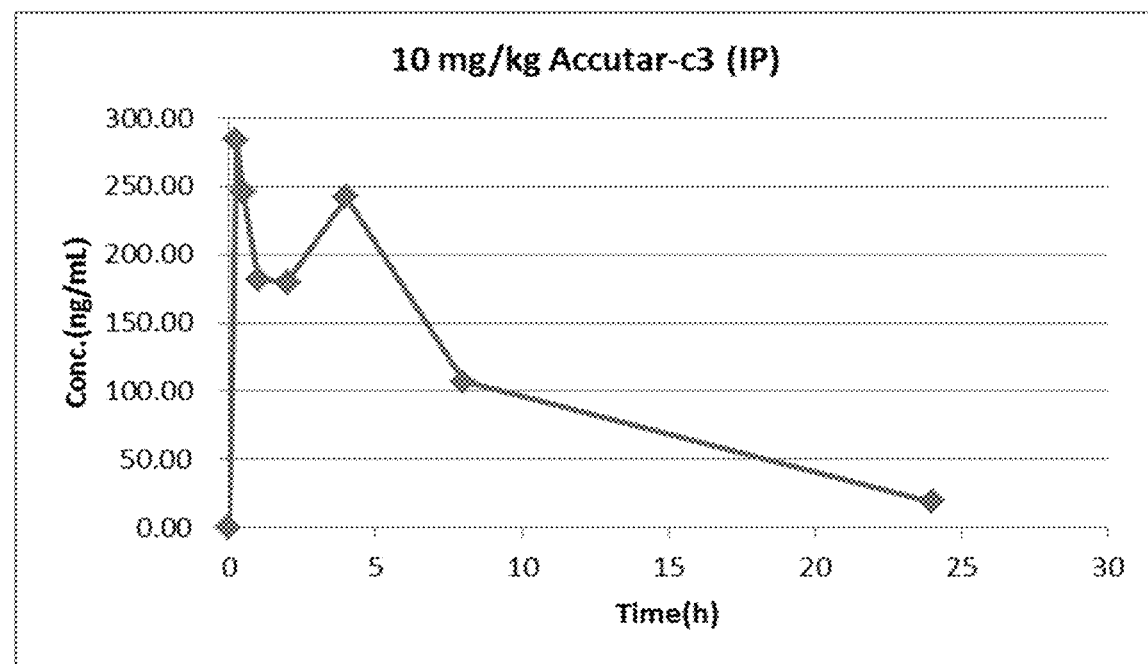
FIG. 13A depicts the blood plasma concentration-time curve after single intraperitoneal injection (IP) of 10 mg/kg C3.
Figure 13B:
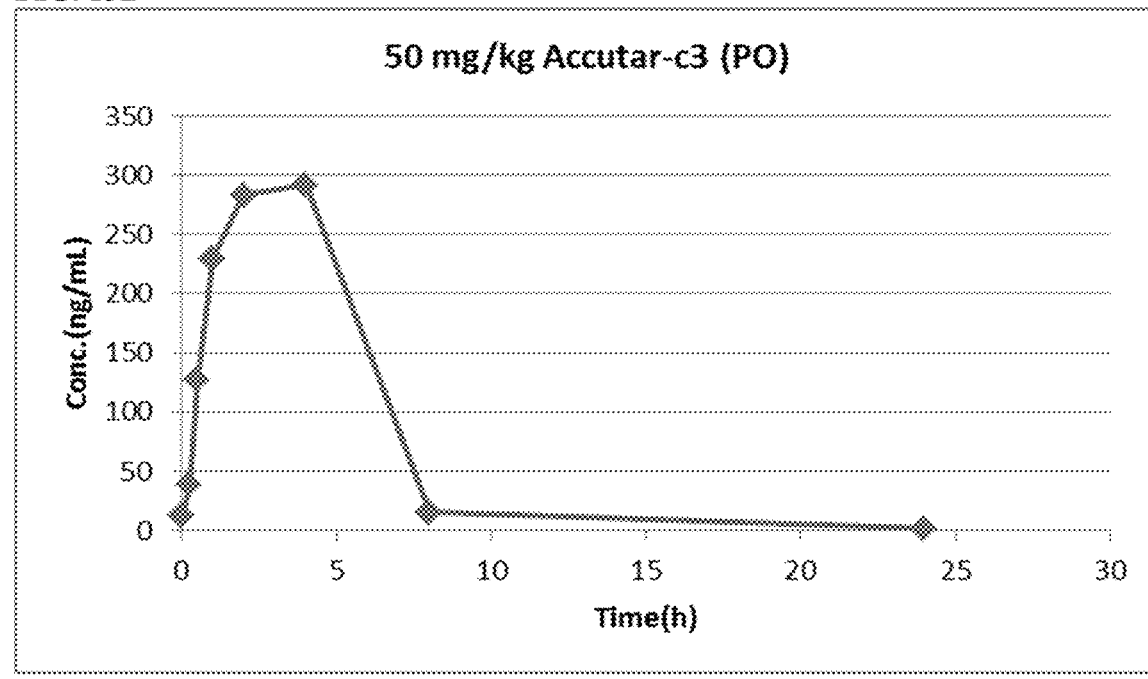
FIG. 13B depicts the blood plasma concentration-time curve after oral administration (PO) of 50 mg/kg C3.

The blood plasma concentration-time curve after single intraperitoneal injection (IP) of 10 mg/kg C3 is provided in FIG. 13A, and the blood plasma concentration-time curve after oral administration (PO) of 50 mg/kg C3 is provided in FIG. 13B.

Biological Example 10. MCF/E2 Xenograft Tumor Model

Figure 14A:
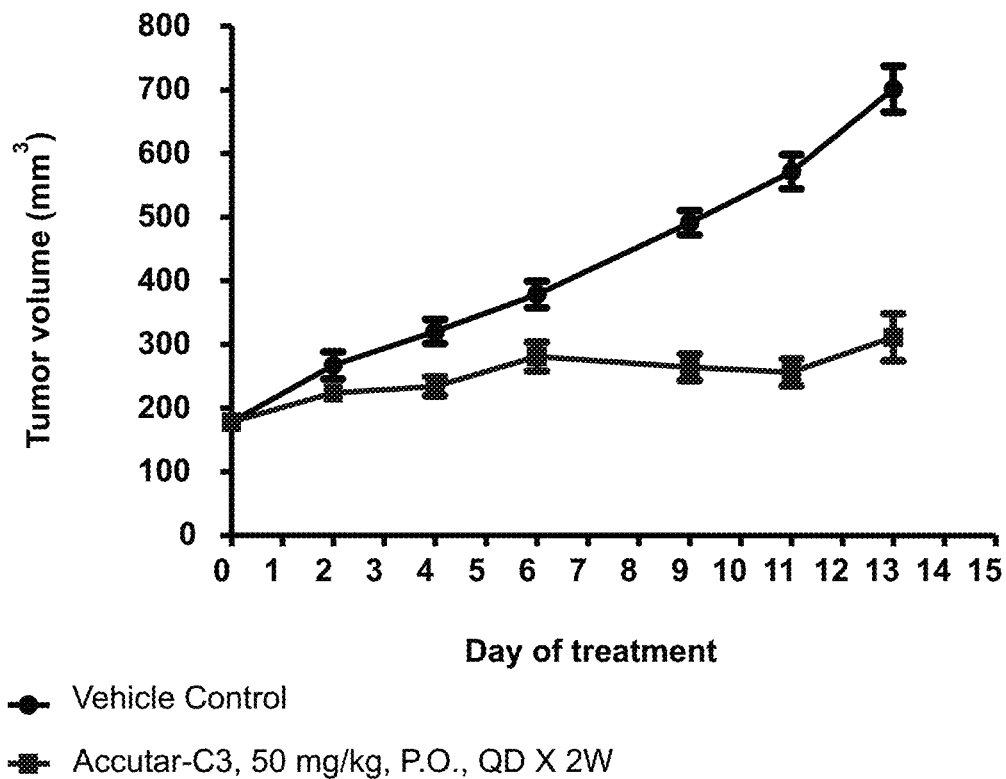
FIG. 14A depicts the change in tumor volume during treatment with C3 compared to a vehicle control in MCF7/E2 xenograft model.
Figure 14B:
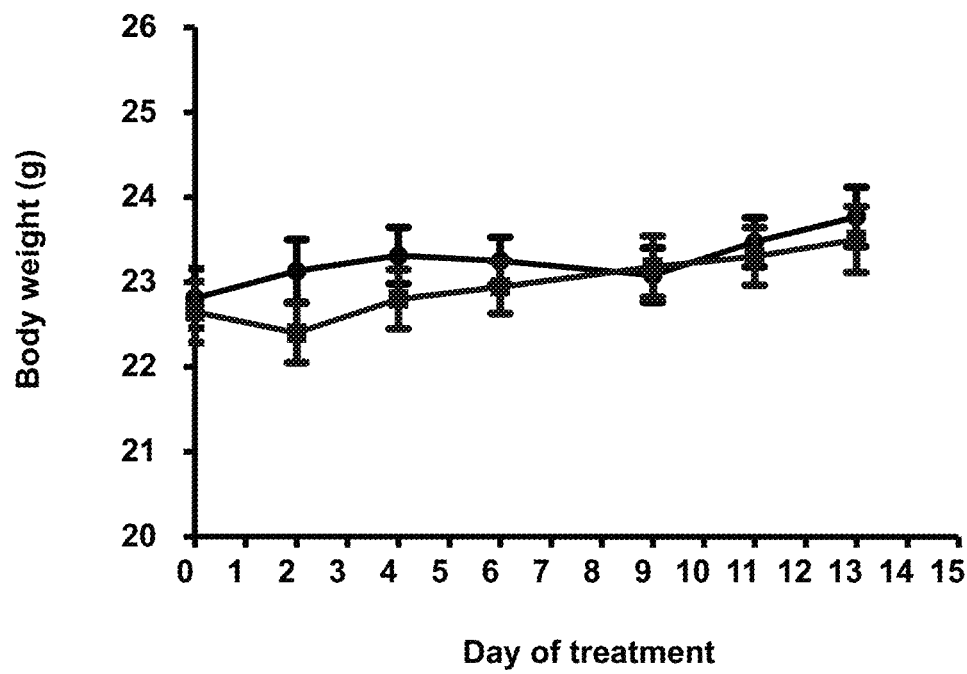
FIG. 14B shows that change in body weight during treatment with C3 compared to a vehicle control in MCF7/E2 xenograft model.

A MCF/E2 xenograft tumor mouse model was used to evaluate the efficacy of C3 in the treatment of breast cancer. 50 mg/kg of C3 was administered, P.O., once daily (QD) for 2 weeks. Data was compared to a vehicle control. FIG. 14A shows the change in tumor volume during treatment with C3 compared to a vehicle control. This data shows that C3 was able to limit tumor growth compared to the vehicle control. FIG. 14B shows that change in body weight during treatment with C3 compared to a vehicle control. This data shows that administration of C3 does not causes changes in body weight.

Biological Example 11. MCF7 and MDA-MB-231 Breast Cancer Cell Assays

MCF7 is a breast cancer cell line isolated from a 69-year-old Caucasian female. MDA-MB-231 is a cell line is an epithelial, human breast cancer cell line that was established from a pleural effusion of a 51-year-old caucasian female with a metastatic mammary adenocarcinomal. Cell assays were performed using increasing concentrations of C3 and cell viability was measured. Olaparib and palbocicilib were also used in the cell assays to compare the efficacy of C3 in decreasing cell viability of these breast cancer lines.

Figure 15A:
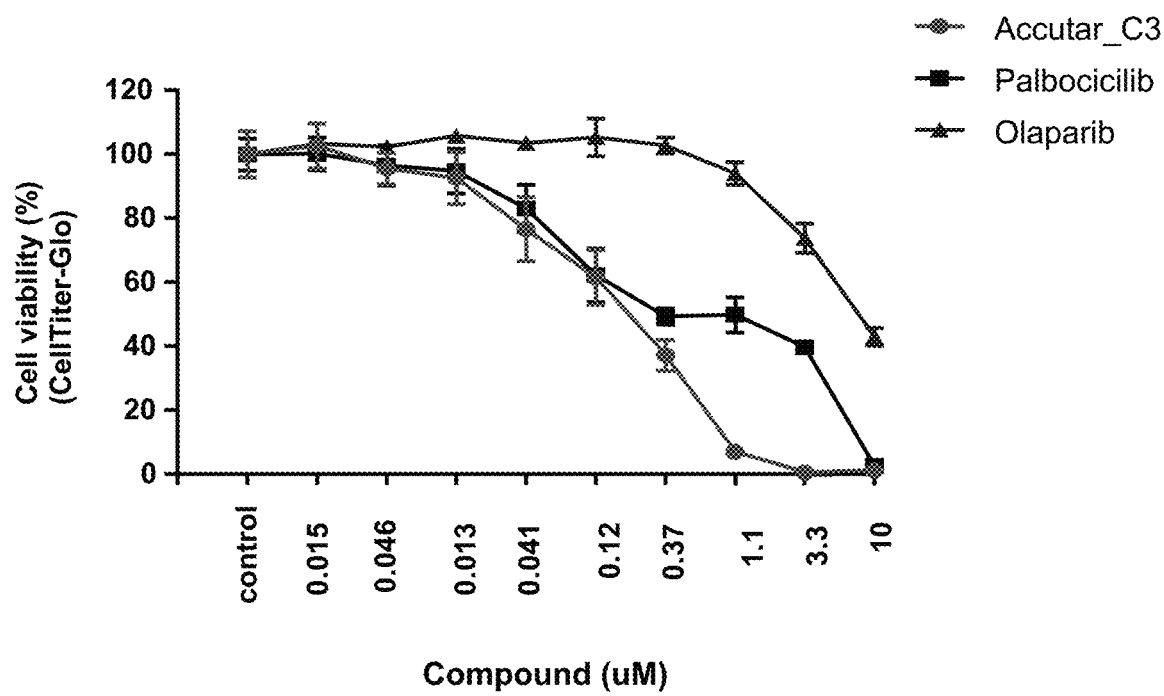
FIG. 15A depicts that C3 reduced cell viability of MCF7 cells at lower concentrations compared to both olaparib and palbocicilib.
Figure 15B:
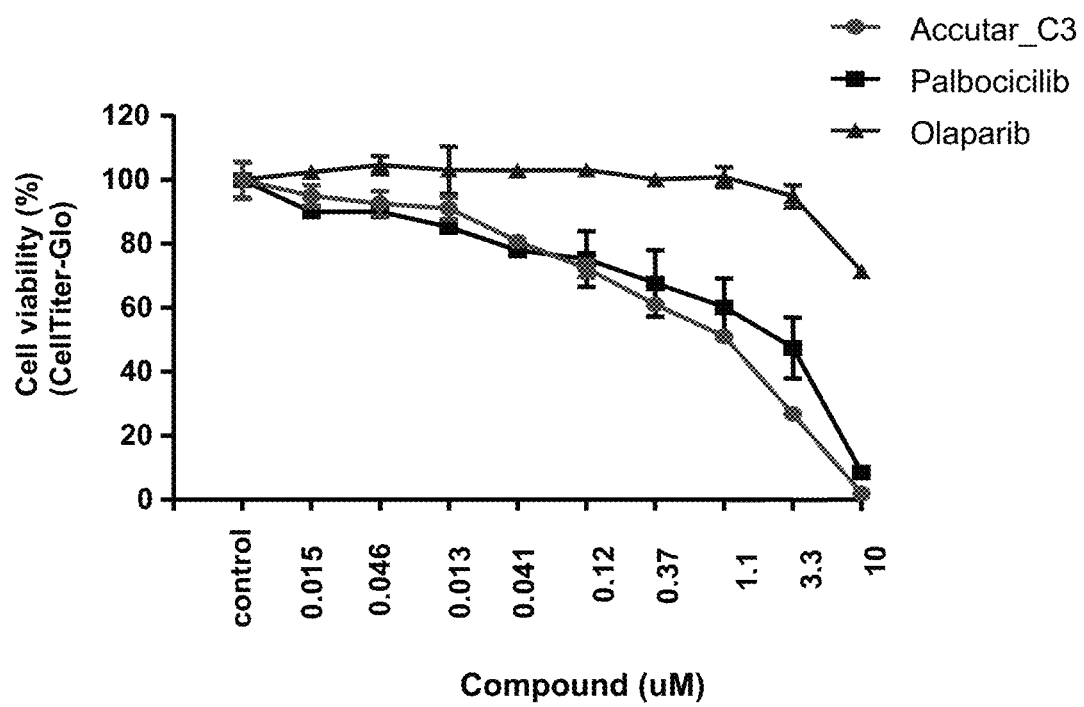
FIG. 15B depicts C3 is more effective in reducing cell viability of MDA-MB-231 cell than olaparib and palbocicilib.

FIG. 15A shows that C3 reduced cell viability of MCF7 cells at lower concentrations compared to both olaparib and palbocicilib. Notably, olaparib did not reduce cell viability to 0% at the concentrations tested, whereas C3 reduced cell viability to 0 between 1.1 and 3.3 µM. FIG. 15B shows that C3 is more effective in reducing cell viability of MDA-NIB-231 cell than olaparib and palbocicilib. Similar to the results observed with MCF cells, C3 was significantly more potent in reducing cell viability than olaparib.

We claim:

1. A compound having a structure according to Formula I,

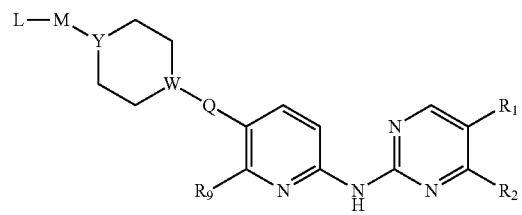

(I)

or a pharmaceutically acceptable salt or tautomer, thereof, wherein:

M is —C(O)—;

L is a carbocyclyl comprising from 3 to 20 carbon atoms optionally substituted with one or more halogen, aryl, 5- to 20-membered heteroaryl comprising one to six heteroatoms selected from the group consisting of N, O, or S, arylalkyl, or heteroarylalkyl comprising a 5- to 20 membered heteroaryl having one to six heteroatoms selected from the group consisting of N, O, or S, wherein the aryl, heteroaryl, arylalkyl, or heteroarylalkyl is optionally substituted with one or more substituents selected from the group consisting of halogen, nitro, hydroxyl, SH, oxo, alkyl, alkenyl, alkynyl, aryl, 3- to 20-membered heterocyclyl comprising one to six heteroatoms selected from the group consisting of N, O, or S, $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSO_2R_g$, $SO_2OR_g$, $=NSO_2R_g$, $SO_2NR_gR_h$, $C(=O)R_g$, $C(=O)OR_g$, $-C(O)NR_gR_h$, $CH_2SO_2R_g$, and $CH_2SO_2NR_gR_h$, wherein each of $R_g$ and $R_h$ are independently hydrogen, alkyl, alkenyl, or alkynyl;

Q is $CH_2$, O, S, or a bond;

W and Y are independently CH or N, provided that at least one of W or Y is N, and when W is CH, Q is O or S;

$R_1$ and $R_2$ are independently selected from hydrogen, halogen, alkyl, and 3- to 20-membered heterocyclyl comprising one to six heteroatoms selected from the group consisting of N, O, or S, wherein the alkyl and heterocyclyl are each optionally substituted with one or more halogen, alkyl, or combinations thereof; and $R_9$ is hydrogen, halogen, or alkyl.

2. A compound having a structure according to Formula II,

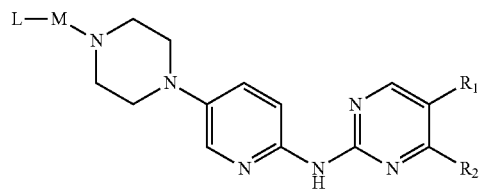

(II)

or a pharmaceutically acceptable salt or tautomer, thereof, wherein:

M is —C(O)—;

L is a carbocyclyl comprising from 3 to 20 carbon atoms, which is optionally substituted with one or more halogen, aryl, 5- to 20-membered heteroaryl comprising one to six heteroatoms selected from the group consisting of N, O, or S, arylalkyl, or heteroarylalkyl comprising a 5- to 20 membered heteroaryl having one to six heteroatoms selected from the group consisting of N, O, or S, wherein the aryl, heteroaryl, arylalkyl, or heteroarylalkyl is optionally substituted with one or more substituents selected from the group consisting of halogen, nitro, hydroxyl, SH, oxo, alkyl, alkenyl, alkynyl, aryl, 3- to 20-membered heterocyclyl comprising one to six heteroatoms selected from the group consisting of N, O, or S, $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSO_2R_g$, $SO_2OR_g$, $=NSO_2R_g$, $SO_2NR_gR_h$, $C(=O)R_g$, $C(=O)OR_g$, $-C(O)NR_gR_h$, $CH_2SO_2R_g$, and $CH_2SO_2NR_gR_h$, wherein each of $R_g$ and $R_h$ are independently hydrogen, alkyl, alkenyl, or alkynyl; and $R_1$ and $R_2$ are independently selected from hydrogen, halogen, alkyl, and 3- to 20-membered heterocyclyl comprising one to six heteroatoms selected from the group consisting of N, O, or S, wherein the alkyl and heterocyclyl are each optionally substituted with one or more halogen, alkyl, or combinations thereof.

3. The compound of claim 2, wherein L is aryl, 5- to 20-membered heteroaryl comprising one to six heteroatoms selected from the group consisting of N, O, or S, arylalkyl, and heteroarylalkyl comprising a 5- to 20-membered heteroaryl having one to six heteroatoms selected from the group consisting of N, O, or S, wherein the aryl, heteroaryl, arylalkyl, and heteroarylalkyl are independently optionally substituted with one or more substituents selected from the group consisting of halogen, nitro, hydroxyl, SH, alkyl, aryl, heterocyclyl, oxo, and $-C(O)NR_gR_h$, wherein each of $R_g$ and $R_h$ are independently hydrogen or alkyl.

4. The compound of claim 2, wherein L is aryl optionally substituted with one or more substituents selected from the group consisting of halogen and heteroarylalkyl, wherein the heteroarylalkyl is optionally substituted with an oxo.

5. The compound of claim 4, wherein the aryl is a $C_{6-8}$ aryl optionally substituted with one or more substituents selected from the group consisting of halogen and 8-12-membered heteroaryl ring having from 1 to 4 atoms independently selected from nitrogen, oxygen and sulfur and wherein the heteroaryl is optionally substituted with one or more substituents selected from the group consisting of halogen, nitro, hydroxyl, SH, alkyl, alkenyl, alkynyl, aryl, 3- to 20-membered heterocyclyl comprising one to six heteroatoms selected from the group consisting of N, O, or S, oxo, $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSO_2R_g$, $SO_2OR_g$, $=NSO_2R_g$, $SO_2NR_gR_h$, $C(=O)R_g$, $C(=O)OR_g$, $-C(O)NR_gR_h$, $CH_2SO_2R_g$, and $CH_2SO_2NR_gR_h$, wherein each of $R_g$ and $R_h$ are independently hydrogen, alkyl, alkenyl, or alkynyl.

6. The compound of claim 5, wherein L is a C6 aryl substituted with fluorine and a 10-membered heteroaryl ring having 2 nitrogen atoms, wherein the heteroaryl is substituted with an oxo group.

7. The compound of claim 1, wherein L is

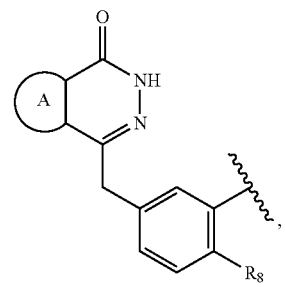

wherein:

the A ring represents a fused aryl or 5- to 20-membered heteroaryl comprising one to six heteroatoms selected from the group consisting of N, O, or S, each of which is optionally substituted with one or more substituent groups selected from halogen, nitro, hydroxyl, SH, amino, alkyl, aryl, and 3- to 20-membered heterocyclyl comprising one to six heteroatoms selected from the group consisting of N, O, or S; and $R_8$ is hydrogen or halogen.

8. The compound of claim 7, wherein the A ring is a $C_{6-8}$ aryl.

9. The compound of claim 8, wherein the A ring is benzene.

10. The compound of claim 7, wherein $R_8$ is —F.

11. The compound of claim 2, wherein $R_1$ is halogen.

12. The compound of claim 2, wherein $R_2$ is a 6-12 membered heteroaryl having from 1 to 4 heteroatoms independently selected from N, O, or S, optionally substituted with one or more halogen or alkyl.

13. The compound of claim 12, wherein $R_2$ is 9-membered heteroaryl having 2 nitrogen atoms substituted with one or more substituents selected from halogen, alkyl, and combinations thereof.

14. The compound of claim 1, wherein $R_2$ is

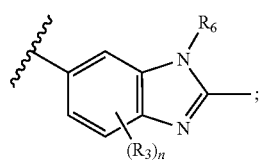

wherein:

n is 0, 1, 2, or 3;

each $R_3$ is independently halogen or alkyl; and $R_6$ is alkyl or cycloalkyl comprising from 3 to 20 carbon atoms, wherein the cycloalkyl is optionally substituted with one or more alkyl.

15. The compound of claim 14, wherein $R_2$ is selected from the group consisting of:

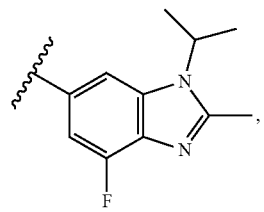

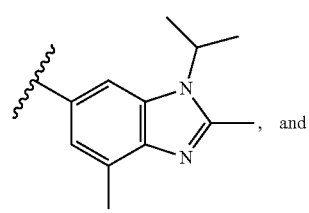, and

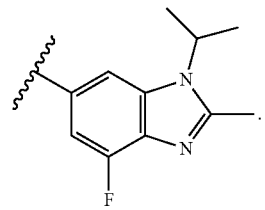 [SMILES: *c1cc(F)c2nc(C)n(C(C)C)c2c1]

16. The compound of claim 15, wherein $R_2$ is:

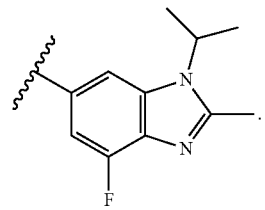 [SMILES: *c1cc(F)c2nc(C)n(C(C)C)c2c1]

17. The compound of claim 1, having the following structure:

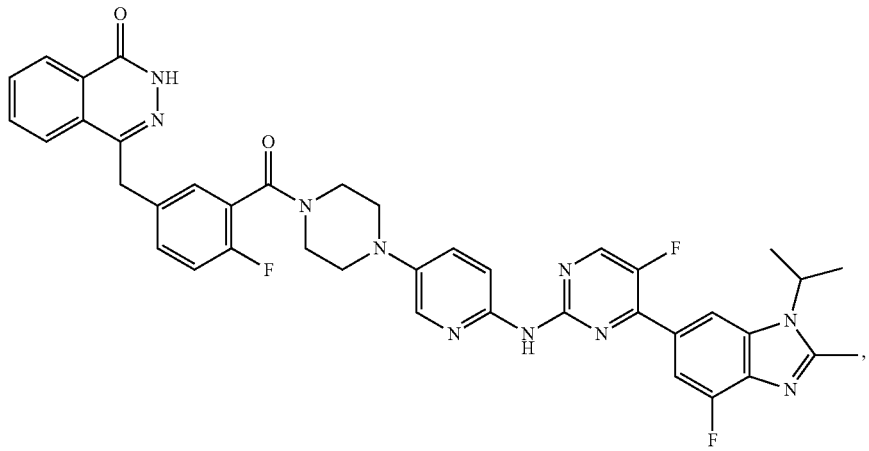 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]

or a pharmaceutically acceptable salt or tautomer, thereof.

18. The compound of claim 2, having the following structure:

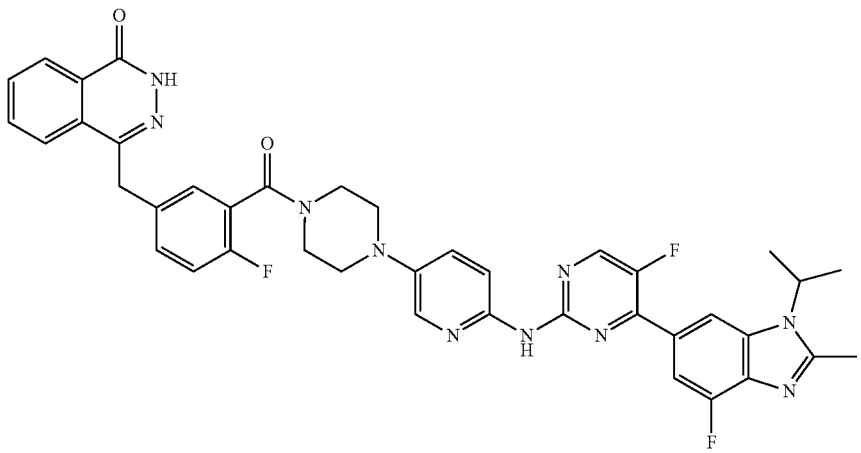 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]

or a pharmaceutically acceptable salt or tautomer, thereof.

19. A pharmaceutical composition comprising the compound of claim 1, and at least one excipient.

20. The pharmaceutical composition of claim 19, wherein the compound has the following structure:

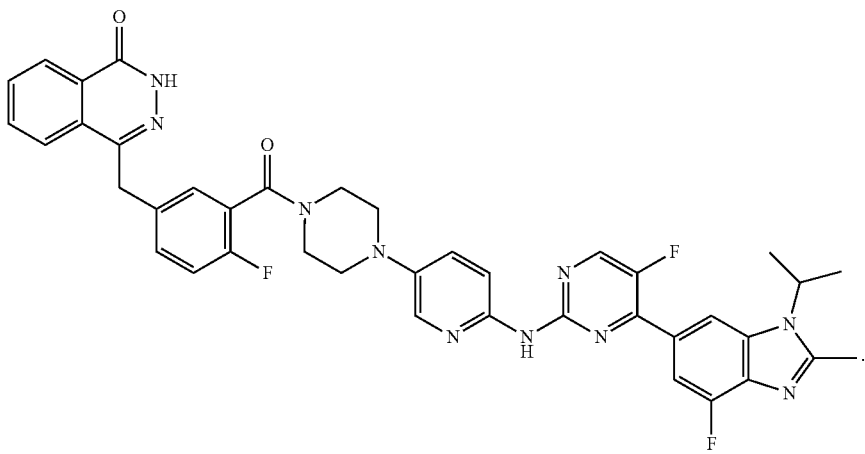 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]

21. A method of treating breast cancer in a patient in need thereof, comprising administering to the patient a therapeutically effective amount of the compound of claim 1, thereby treating breast cancer.

22. The method of claim 21, wherein the breast cancer is hormone receptor (HR)-positive breast cancer human epidermal growth factor receptor 2 (HER2)-negative advanced, or metastatic breast cancer.

23. The method of claim 21, wherein the breast cancer is triple negative breast cancer (TNBC).

24. The method of claim 21, wherein the breast cancer is estrogen-receptor positive breast cancer.

25. The method of claim 21, wherein the breast cancer is BRAC1 triple negative breast cancer.

26. The method of claim 21, wherein the compound has the following structure:
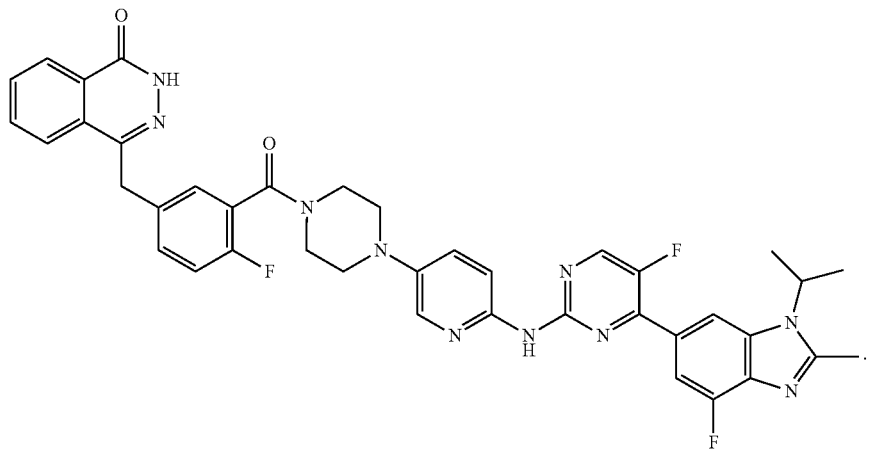 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]
27. The compound of claim 1, having following structure:
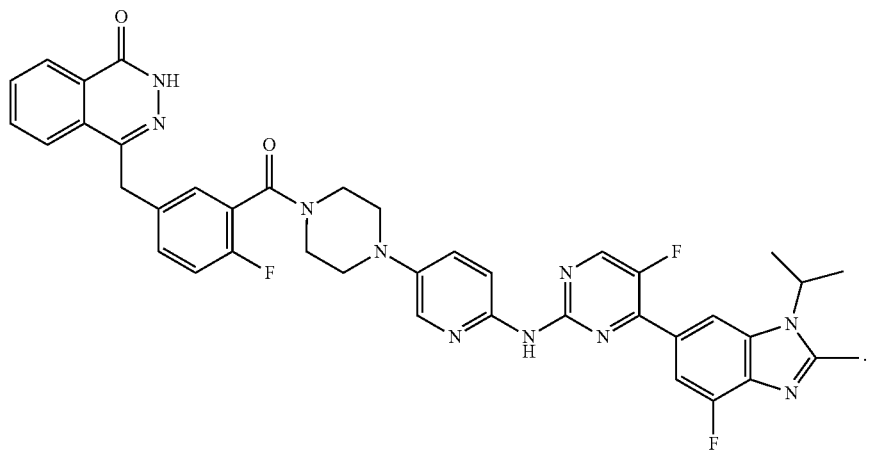 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]
45
28. The compound of claim 2, having following structure:
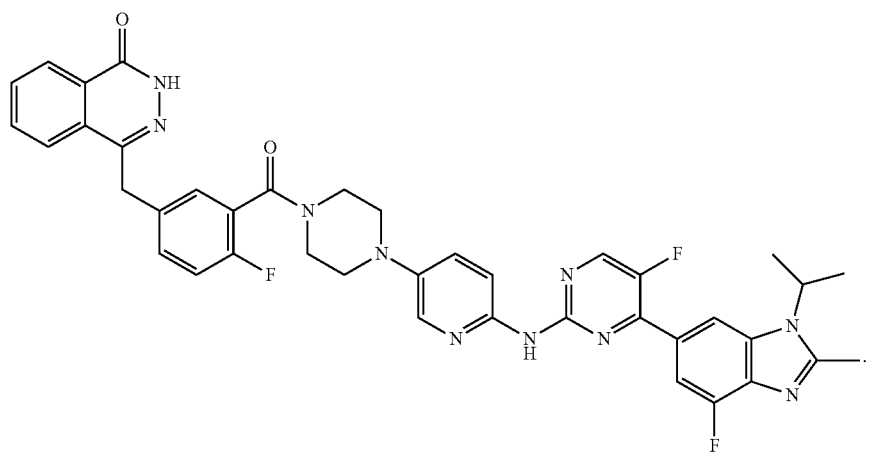 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]

29. The method of claim 21, wherein the compound has the following structure:
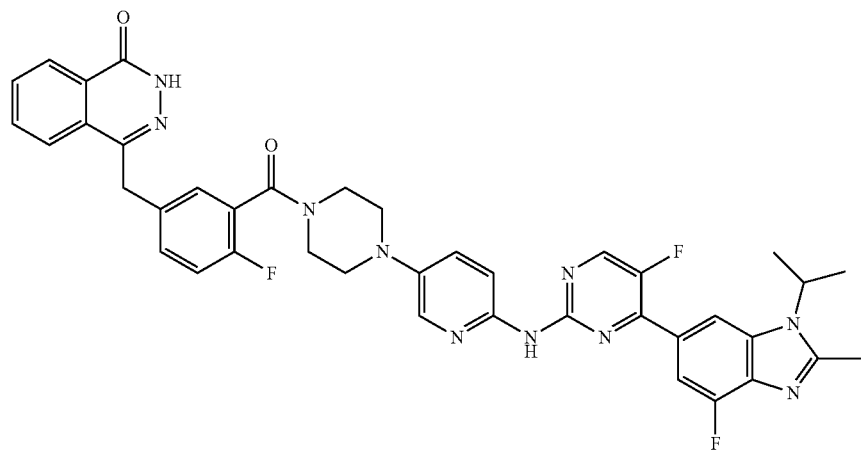 [SMILES: Cc1nc2c(F)cc(-c3nc(Nc4ccc(N5CCN(C(=O)c6cc(Cc7n[nH]c(=O)c8ccccc78)ccc6F)CC5)cn4)ncc3F)cc2n1C(C)C]
or a pharmaceutically acceptable salt or tautomer, thereof.
* * * * *